US010626148B2

(12) United States Patent
Haldar et al.

(10) Patent No.: US 10,626,148 B2
(45) Date of Patent: Apr. 21, 2020

(54) GLYCOPEPTIDES CONJUGATES AND USES THEREOF

(71) Applicant: JAWAHARLAL NEHRU CENTRE FOR ADVANCED SCIENTIFIC RESEARCH (JNCASR), Bangalore (IN)

(72) Inventors: Jayanta Haldar, Bangalore (IN); Venkateswarlu Yarlagadda, Bangalore (IN)

( * ) Notice: Subject to any disclaimer, the term of this patent is extended or adjusted under 35 U.S.C. 154(b) by 0 days.

(21) Appl. No.: 15/549,086

(22) PCT Filed: Feb. 5, 2016

(86) PCT No.: PCT/IN2016/050047
§ 371 (c)(1),
(2) Date: Aug. 4, 2017

(87) PCT Pub. No.: WO2016/125193
PCT Pub. Date: Aug. 11, 2016

(65) Prior Publication Data
US 2018/0009848 A1    Jan. 11, 2018

(30) Foreign Application Priority Data
Feb. 6, 2015    (IN) .............................. 605/CHE/2015

(51) Int. Cl.
*C07K 9/00*    (2006.01)
*A61K 38/00*    (2006.01)
*A61K 38/14*    (2006.01)

(52) U.S. Cl.
CPC .............. *C07K 9/008* (2013.01); *A61K 38/14* (2013.01); *A61K 38/00* (2013.01)

(58) Field of Classification Search
CPC ........ C07K 9/008; C07K 7/06; C07K 1/1075; C07K 1/13; A61K 38/00; A61K 38/14; A61K 47/61; A61K 51/088
See application file for complete search history.

(56) References Cited

FOREIGN PATENT DOCUMENTS

WO    WO-2013072838 A1 *    5/2013 ............. C07K 9/008

OTHER PUBLICATIONS

Deresinski, Clinical Infectious Diseases, 2009; 49:1072-9. (Year: 2009).*

* cited by examiner

*Primary Examiner* — James H Alstrum-Acevedo
*Assistant Examiner* — Kaipeen E Yang
(74) *Attorney, Agent, or Firm* — Stites & Harbison, PLLC; Mandy Wilson Decker

(57) ABSTRACT

Vancomycin conjugates of Formula I, its stereoisomers, prodrugs, pharmaceutically acceptable salts, and metal coordination complexes thereof is described in the present disclosure. Further, the present disclosure relates to pharmaceutical compositions comprising vancomycin conjugates, its stereoisomers, prodrugs, pharmaceutically 10 acceptable salts, metal coordination complex thereof with one or more other pharmaceutical compositions or an antibiotic. The present disclosure also describes a process of preparing said conjugates, its stereoisomers, prodrugs, pharmaceutically acceptable salts, and metal coordination complex thereof, and pharmaceutical compositions as described above. Furthermore, the present disclosure describes 15 compositions and methods of treating conditions and diseases that are mediated by bacteria.

Formula I

17 Claims, 3 Drawing Sheets

GLYCOPEPTIDES CONJUGATES AND USES THEREOF

FIELD OF INVENTION

The present disclosure relates to the field of medicinal chemistry and more particularly to the development of antibacterial compounds. The present disclosure particularly relates to vancomycin conjugates, its stereoisomers, prodrugs, pharmaceutically acceptable salts, and metal coordination complexes thereof. The present disclosure also relates to pharmaceutical compositions comprising vancomycin conjugates, its stereoisomers, prodrugs, pharmaceutically acceptable salts, metal coordination complex thereof with one or more other pharmaceutical compositions or an antibiotic. The present disclosure further relates to a process of preparing said conjugates, its stereoisomers, prodrugs, pharmaceutically acceptable salts, and metal coordination complex thereof, and pharmaceutical compositions as described above. The present disclosure also relates to compositions and methods of treating conditions and diseases that are mediated by bacteria.

BACKGROUND

Infectious diseases are one of the leading causes of death in the world. The problem of infectious diseases is exacerbated by the prevalence of multidrug-resistance in bacteria.[1] Vancomycin is a glycopeptide antibiotic that has become drug of last resort to treat life-threatening bacterial infections such as those caused by methicillin-resistant S. aureus (MRSA).[2,3] Vancomycin binds to D-Ala-D-Ala terminus of peptidoglycan pentapeptide of the bacterial cell wall, thus inhibiting transpeptidase-catalyzed cross-linking and maturation of the bacterial cell wall.[2] However, bacteria have acquired resistance to vancomycin by alteration of cell wall precursors from D-Ala-D-Ala to D-Ala-D-Lac (vancomycin-resistant Enterococci, VRE), thickening of the cell wall (vancomycin intermediate resistant S. aureus, VISA) or sometimes modifying both (vancomycin-resistant S. aureus, VRSA).[2,4,5] The alteration of the precursor is exhibited by five van genes and leads to manifold reduction in the binding constant of vancomycin to its target and results in loss of antibacterial activity.[4] This perennial persistence of vancomycin resistance calls for urgent measures to develop more potent analogues. Hence, this persistent threat of drug resistance has triggered the scientific community all over the world to develop various strategies to tackle the problem. Currently, semi-synthetic glycopeptides; telavancin, dalbavancin and oritavancin are already approved for the treatment of skin infections caused by methicillin-resistant *Staphylococcus aureus* (MRSA).[2]

Gram negative bacterial infections also pose an equal threat to human life. The WHO Global Report on Surveillance of Antimicrobial Resistance 2014 describes that gram negative bacteria like *E. coli* and *K. pneumoniae* have developed more than 50% of resistance to commonly used antibacterial drugs.[6,7] More importantly, carbepenem-resistant bacteria, such as New Delhi Metallo β-lactamase-I (NDM-1) bacteria have become resistant to even last line of antibiotics, such as colistin.[6,7]

Thus, there is an urgent need to develop novel strategy to overcome the resistance of gram positive bacteria. Also, it is vital to widen therapeutic options for the treatment of gram negative bacterial infections.

SUMMARY

The present disclosure provides a compound of Formula I

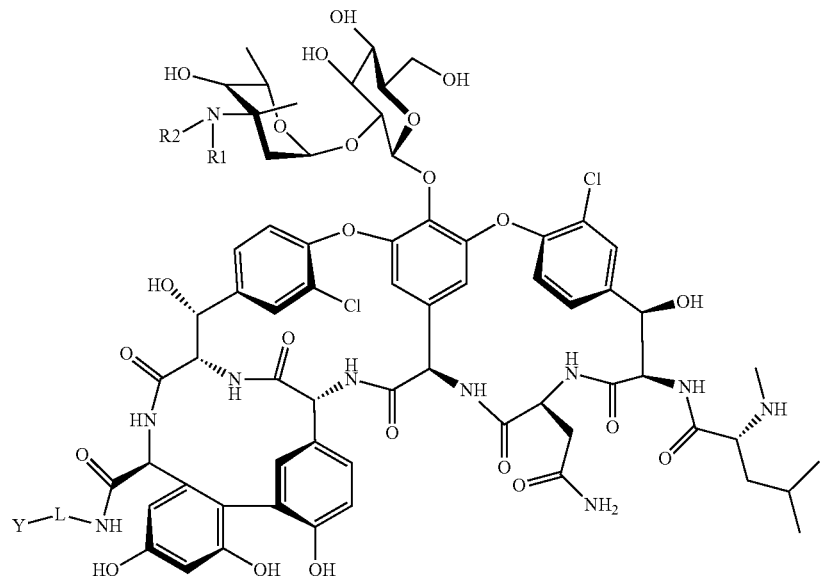

Formula I its stereoisomers, prodrugs, or pharmaceutically acceptable salts, and a metal coordination complex thereof:

wherein $R^1$ and $R^2$ are independently selected from hydrogen, substituted or unsubstituted $C_1$-$C_{18}$ aliphatic radical or substituted or unsubstituted $C_4$-$C_{18}$ aromatic radical;

L is selected from substituted or unsubstituted $C_1$-$C_{18}$ aliphatic radical or substituted or unsubstituted $C_4$-$C_{18}$ aromatic radical; and Y is selected from $NR^3R^4$ or substituted $C_4$-$C_{18}$ aromatic radical, wherein $R^3$ and $R^4$ are independently selected from substituted $C_1$-$C_{18}$ aliphatic radical or substituted $C_4$-$C_{18}$ aromatic radical.

The present disclosure further relates to a pharmaceutical composition comprising a compound of Formula I, its stereoisomers, prodrugs, or pharmaceutically acceptable salts, and a metal coordination complex thereof and an antibiotic.

The present disclosure further relates to a compound of Formula I, its stereoisomers, prodrugs, or pharmaceutically acceptable salts, and a metal coordination complex thereof or a pharmaceutical composition comprising a compound of Formula I, its stereoisomers, prodrugs, or pharmaceutically acceptable salts, and a metal coordination complex thereof and an antibiotic, for use as a medicament.

The present disclosure also relates to a compound of Formula I, its stereoisomers, prodrugs, or pharmaceutically acceptable salts, and a metal coordination complex thereof or a pharmaceutical composition comprising a compound of Formula I, its stereoisomers, prodrugs, or pharmaceutically acceptable salts, and a metal coordination complex thereof and an antibiotic, for use in a treatment of a bacterial infection.

The present disclosure relates to a method for the treatment of bacterial infection in a subject comprising: administering to the subject an effective amount of a compound of Formula I, its stereoisomers, prodrugs, or pharmaceutically acceptable salts, and a metal coordination complex thereof or a pharmaceutical composition comprising a compound of Formula I, its stereoisomers, prodrugs, or pharmaceutically acceptable salts, and a metal coordination complex thereof and an antibiotic.

The present disclosure further relates to a pharmaceutical composition comprising a compound of Formula I or its stereoisomers, prodrugs pharmaceutically acceptable salts, and a metal coordination complex thereof, together with a pharmaceutically acceptable carrier.

The present disclosure relates to a process for preparation of a compound of Formula I, its stereoisomers, prodrugs, or pharmaceutically acceptable salts, and a metal coordination complex thereof or a pharmaceutical composition comprising a compound of Formula I, its stereoisomers, prodrugs, or pharmaceutically acceptable salts, and a metal coordination complex thereof and an antibiotic.

These and other features, aspects, and advantages of the present subject matter will become better understood with reference to the following description. This summary is provided to introduce a selection of concepts in a simplified form. This summary is not intended to identify key features or essential features of the disclosure, nor is it intended to be used to limit the scope of the subject matter.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to reference like features and components.

DETAILED DESCRIPTION

Figure 1:
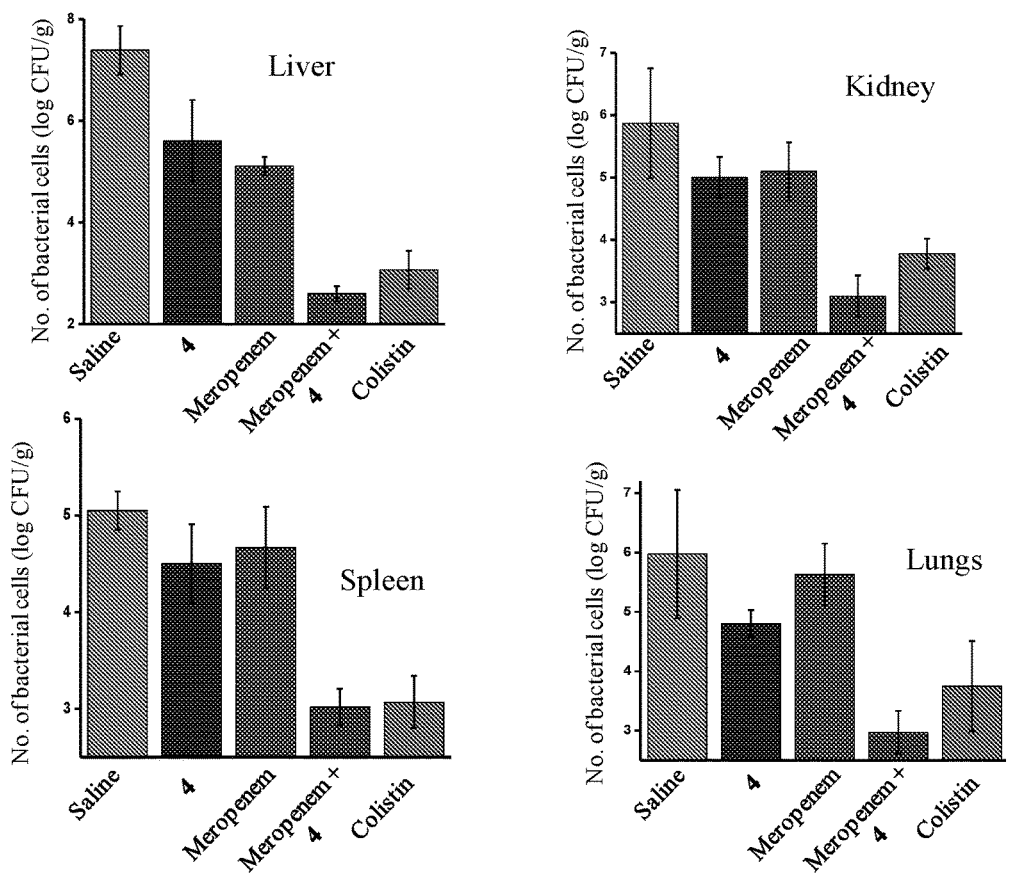
FIG. 1 illustrates In-vivo antibacterial activity against *Klebsiella pneumoniae* sepsis infection model.

In the structural formulae given herein and throughout the present disclosure, the following terms have been indicated meaning, unless specifically stated otherwise.

Definitions

The term "alkyl" or "unsubstituted $C_1$-$C_{18}$ aliphatic radical" refers to a monoradical branched or unbranched saturated hydrocarbon chain having from 1 to 18 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" or "substituted $C_1$-$C_{18}$ aliphatic radical" refers to an alkyl group as defined above, having 1, 2, 3, or 4 substituents, preferably 1, 2 or 3 substituents, selected from the group consisting of alkyl, alkenyl, alkynyl, alkoxy, acyl, acyloxy, acylamino, amino, monoalkylamino, dialkylamino, trialkylamino, halogen, hydroxy, hydroxyalkyl, keto, thiocarbonyl, carboxy, alkylcarboxy, hydroxyamino, alkoxyamino, nitro, azido, cyano, cycloalkyl, cycloalkylalkyl, aryl, arylalkyl, heterocyclyl, heterocyclylalkyl, heteroaryl, heteroarylalkyl, cycloalkenyl, cycloalkylamino, arylamino, heterocyclylamino, heteroarylamino, cycloalkyloxy, aryloxy, heterocyclyloxy or heteroaryloxy.

The term "alkenyl" refers to a monoradical of a branched or unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 2, 3, 4, 5 or 6 double bond (vinyl), preferably 1 double bond. Preferred alkenyl groups include ethenyl or vinyl (—CH═$CH_2$), 1-propylene or allyl (—$CH_2$CH═$CH_2$), isopropylene (—C($CH_3$)═$CH_2$), bicyclo [2.2.1] heptene, and the like.

The term "substituted alkenyl" refers to an alkenyl group as defined above having 1, 2, 3, or 4 substituents, and preferably 1, 2, or 3 substituents, selected from the group consisting of alkyl, alkenyl, alkynyl, alkoxy, acyl, acyloxy, acylamino, amino, halogen, hydroxy, hydroxyalkyl, keto, thiocarbonyl, carboxy, alkylcarboxy, hydroxyamino, alkoxyamino, nitro, azido, cyano, cycloalkyl, cycloalkylalkyl, aryl, arylalkyl, heterocyclyl, heterocyclylalkyl, heteroaryl, heteroarylalkyl, cycloalkenyl, cycloalkylamino, arylamino, heterocyclylamino, heteroarylamino, cycloalkyloxy, aryloxy, heterocyclyloxy or heteroaryloxy;

The term "alkynyl" refers to a monoradical of an unsaturated hydrocarbon, preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 2, 3, 4, 5 or 6 sites of acetylene (triple bond) unsaturation, preferably 1 triple bond. Preferred alkynyl groups include ethynyl, (—C≡CH), propargyl (or prop-1-yn-3-yl-$CH_2$C≡CH), homopropargyl (or but-1-yn-4-yl, —$CH_2CH_2$C≡CH) and the like.

The term "substituted alkynyl" refers to an alkynyl group as defined above having 1, 2, 3, or 4 substituents, and preferably 1, 2, or 3 substituents, selected from the group consisting of alkyl, alkenyl, alkynyl, alkoxy, acyl, acyloxy, acylamino, amino, halogen, hydroxy, hydroxyalkyl, keto, thiocarbonyl, carboxy, alkylcarboxy, hydroxyamino, alkoxyamino, nitro, azido, cyano, cycloalkyl, cycloalkylalkyl, aryl, arylalkyl, heterocyclyl, heterocyclylalkyl, heteroaryl, heteroarylalkyl, cycloalkenyl, cycloalkylamino, arylamino, heterocyclylamino, heteroarylamino, cycloalkyloxy, aryloxy, heterocyclyloxy or heteroaryloxy;

"Halo" or "Halogen", alone or in combination with any other term means halogens such as chloro (Cl), fluoro (F), bromo (Br) and iodo (I).

"Haloalkyl" refers to a straight chain or branched chain haloalkyl group with 1 to 6 carbon atoms. The alkyl group may be partly or totally halogenated. Representative examples of haloalkyl groups include but are not limited to fluoromethyl, chloromethyl, bromomethyl, difluoromethyl, dichloromethyl, dibromomethyl, trifluoromethyl, trichloromethyl, 2-fluoroethyl, 2-chloroethyl, 2-bromoethyl, 2,2,2-trifluoroethyl, 3-fluoropropyl, 3-chloropropyl, 3-bromopropyl and the like.

The term "substituted or unsubstituted $C_4$-$C_{18}$ aromatic radical" refers to a substituted or unsubstituted $C_4$-$C_{18}$ "aryl" or "heteroaryl". The term "aryl" refers to an aromatic carbocyclic group of 4 to 18 carbon atoms having a single ring (e.g. phenyl) or multiple rings (e.g. biphenyl), or multiple condensed (fused) rings (e.g. naphthyl or anthranyl). Preferred aryls include phenyl, naphthyl and the like.

The term "substituted aryl" refers to an aryl group as defined above having 1, 2, 3, or 4 substituents, and preferably 1, 2, or 3 substituents, selected from the group consisting of alkyl, alkenyl, alkynyl, alkoxy, acyl, acyloxy, acylamino, amino, halogen, hydroxy, hydroxyalkyl, keto, thiocarbonyl, carboxy, alkylcarboxy, hydroxyamino, alkoxyamino, nitro, azido, cyano, cycloalkyl, cycloalkylalkyl, aryl, arylalkyl, heterocyclyl, heterocyclylalkyl, heteroaryl, heteroarylalkyl, cycloalkenyl, cycloalkylamino, arylamino, heterocyclylamino, heteroarylamino, cycloalkyloxy, aryloxy, heterocyclyloxy or heteroaryloxy.

The term "arylalkyl" refers to an aryl group covalently linked to an alkylene group, where aryl and alkylene are defined herein.

The term "hydroxyalkyl" refers to the groups-alkylene-OH.

The term "carboxyalkyl" refers to the groups-alkylene-C(O)OH.

The term "cycloalkyl" refers to carbocyclic groups of from 3 to 20 carbon atoms having a single cyclic ring or multiple condensed rings which may be partially unsaturated. Such cycloalkyl groups include, by way of example, single ring structures such as cyclopropyl, cyclobutyl, cyclopentyl, cyclopentenyl, cyclohexyl, cyclohexenyl, cyclooctyl, and the like, or multiple ring structures such as adamantanyl, bicyclo[2.2.1]heptane, 1,3,3-trimethylbicyclo[2.2.1]hept-2-yl, (2,3,3-trimethylbicyclo[2.2.1]hept-2-yl), or carbocyclic groups to which is fused an aryl group, for example indane, and the like.

The term "substituted cycloalkyl" refers to cycloalkyl groups having 1, 2, 3, or 4 substituents, and preferably 1, 2, or 3 substituents, selected from the group consisting of alkyl, alkenyl, alkynyl, alkoxy, acyl, acyloxy, acylamino, amino, halogen, hydroxy, hydroxyalkyl, keto, thiocarbonyl, carboxy, alkylcarboxy, hydroxyamino, alkoxyamino, nitro, azido, cyano, cycloalkyl, cycloalkylalkyl, aryl, arylalkyl, heterocyclyl, heterocyclylalkyl, heteroaryl, heteroarylalkyl, cycloalkenyl, cycloalkylamino, arylamino, heterocyclylamino, heteroarylamino, cycloalkyloxy, aryloxy, heterocyclyloxy or heteroaryloxy.

"Cycloalkylalkyl" refers to an alkyl radical as defined above which is substituted by a cycloalkyl radical as defined above. Representative examples of cycloalkylalkyl include but are not limited to cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl and the like.

The term "heterocyclyl" refers to a saturated or partially unsaturated group having a single ring or multiple condensed rings, having from 1 to 40 carbon atoms and from 1 to 10 hetero atoms, preferably 1, 2, 3 or 4 heteroatoms, selected from nitrogen, sulfur, phosphorus, and/or oxygen within the ring. Heterocyclic groups can have a single ring or multiple condensed rings, and include tetrahydrofuranyl, morpholinyl, piperidinyl, piperazinyl, dihydropyridinyl, tetrahydroquinolinyl, pyrrolidinyl and the like.

The term "heterocyclylalkyl" refers to a heterocyclyl group covalently linked to an alkylene group, where heterocyclyl and alkylene are defined herein.

The term "heteroaryl" refers to an aromatic cyclic group having 4, 5, 6, 7, 8, 9, 10, 11, 12, 13, 14, 15, 16, 17, or 18 carbon atoms and 1, 2, 3 or 4 heteroatoms selected from oxygen, nitrogen and sulfur within at least one ring (if there is more than one ring). Such heteroaryl groups can have a single ring (e.g. pyridyl or furyl) or multiple condensed rings (e.g. indolizinyl, benzothiazolyl, or benzothienyl). Examples of heteroaryls include, but are not limited to, [1,2,4] oxadiazole, [1,3,4] oxadiazole, [1,2,4] thiadiazole, [1,3,4] thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, quinoxaline, quinazoline, cinnoline, pteridine, carbazole, carboline, phenanthridine, acridine, phenanthroline, isothiazole, phenazine, isoxazole, phenoxazine, phenothiazine, furan, thiophene, oxazole, thiazole, triazole, triazine and the like.

The compounds described herein may contain one or more chiral centers and/or double bonds and therefore, may exist as stereoisomers, such as double-bond isomers (i.e., geometric isomers), regioisomers, enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the person skilled in the art. The compounds may also exist in several tautomeric forms including the enol form, the keto form and mixtures thereof. Accordingly, the chemical structures depicted herein encompass all possible tautomeric forms of the illustrated or identified compounds.

The term "prodrug" refers to an inactive, bioreversible derivatives of a compound of Formula I that must undergo an enzymatic and/or chemical transformation in vivo to release the active compound of Formula I, which can then elicit its desired pharmacological effect in the body.

"Pharmaceutically acceptable salt" embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

"Glycopeptide" refers to a heptapeptide antibiotics characterized by a multi-ring peptide core substituted with a saccharide groups.

The term "peptide" refers to a compound consisting of two or more amino acids linked in a chain, the carboxyl group of each acid being joined to the amino group.

The term "metal coordination complex" refers to coordination complex that is the product of a Lewis acid-base reaction in which neutral molecules or anions (called ligands) bond to a central metal atom (or ion) by coordinate covalent bonds.

"Vancomycin" refers to the glycopeptide class of antibiotic having the structural formula

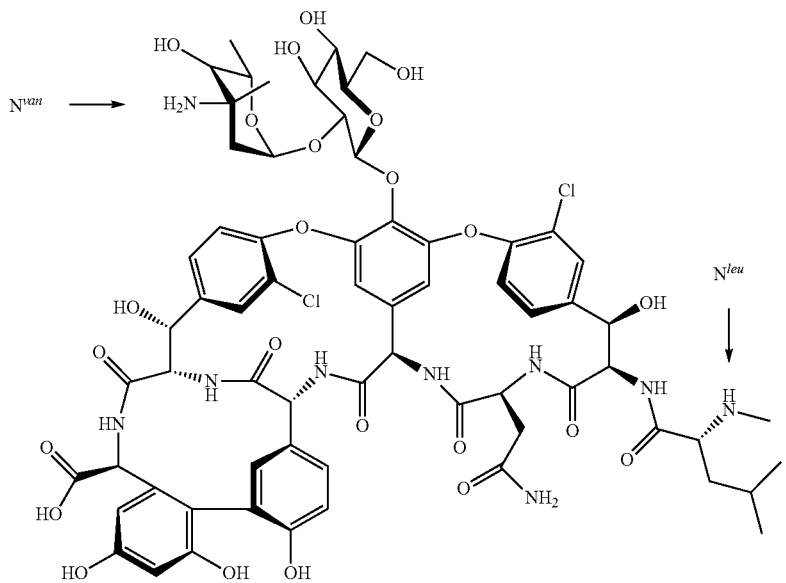

and is also represented in the disclosure by the formula provided below:

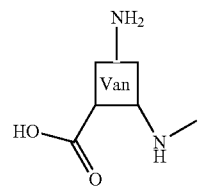

wherein —$NH_2$, —$NHCH_3$ represents $N^{van}$, and $N^{len}$ respectively.

Vancosamine moiety of vancomycin is shown as the N-site where a substituent can be covalently attached to the structure of Vancomycin. Glycopeptide antibiotic vancomycin is one of the antibiotics of last resort used in the treatment of life-threatening infections caused by gram positive bacteria. The present disclosure particularly relates to dipicolyl-vancomycin conjugates and their pharmaceutical compositions. The compounds of the instant disclosure exhibit very high antibacterial activity against vancomycin-resistant enterococci and staphylococci. Also, dipicolyl-vancomycin conjugates resensitized carbapenem antibiotics to carbapenem-resistant gram negative bacteria.

The present disclosure provides a compound of Formula I

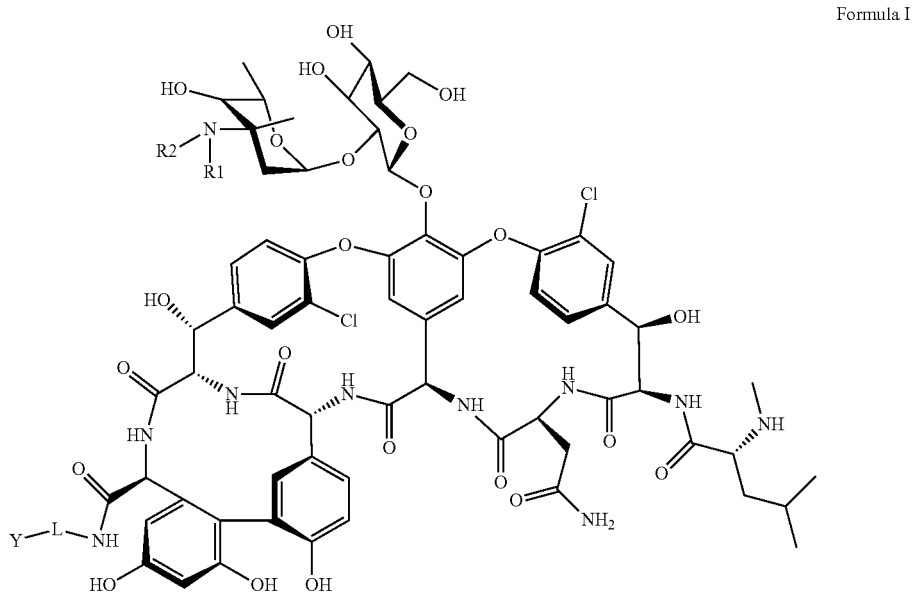

Formula I its stereoisomers, prodrugs, or pharmaceutically acceptable salts, its stereoisomers, prodrugs, or pharmaceutically acceptable salts thereof:
wherein $R^1$ and $R^2$ are independently selected from hydrogen, substituted or unsubstituted $C_1$-$C_{18}$ aliphatic radical, or substituted or unsubstituted $C_4$-$C_{18}$ aromatic radical;
L is selected from substituted or unsubstituted $C_1$-$C_{18}$ aliphatic radical or substituted or unsubstituted $C_4$-$C_{18}$ aromatic radical; and Y is selected from $NR^3R^4$ or substituted $C_4$-$C_{18}$ aromatic radical, wherein $R^3$ and $R^4$ are independently selected from substituted $C_1$-$C_{18}$ aliphatic radical or substituted $C_4$-$C_{18}$ aromatic radical.

According to an embodiment, the present disclosure relates to compounds of Formula II

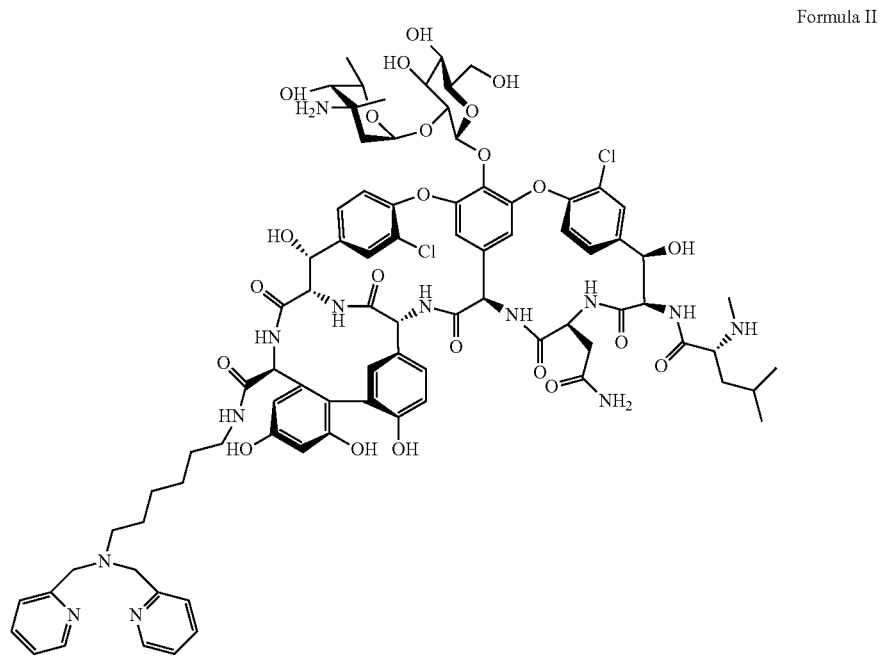

Formula II its stereoisomers, prodrugs, or pharmaceutically acceptable salts thereof.

According to an embodiment, the present disclosure relates to compounds of Formula I, its stereoisomers, prodrugs, or pharmaceutically acceptable salts thereof:
wherein $R^1$ and $R^2$ are independently selected from hydrogen, or substituted or unsubstituted $C_1$-$C_{18}$ aliphatic radical;
L is selected from substituted or unsubstituted $C_1$-$C_{18}$ aliphatic radical or substituted or unsubstituted $C_4$-$C_{18}$ aromatic radical; and
Y is selected from $NR^3R^4$ or substituted $C_4$-$C_{18}$ aromatic radical, wherein $R^3$ and $R^4$ are independently selected from substituted $C_1$-$C_{18}$ aliphatic radical or substituted $C_4$-$C_{18}$ aromatic radical.

According to an embodiment, the present disclosure relates to compounds of Formula I, its stereoisomers, prodrugs, or pharmaceutically acceptable salts, its stereoisomers, prodrugs, or pharmaceutically acceptable salts thereof:
wherein $R^1$ and $R^2$ are independently selected from hydrogen, or substituted or unsubstituted $C_4$-$C_{18}$ aromatic radical;
L is selected from substituted or unsubstituted $C_1$-$C_{18}$ aliphatic radical or substituted or unsubstituted $C_4$-$C_{18}$ aromatic radical; and
Y is selected from $NR^3R^4$ or substituted $C_4$-$C_{18}$ aromatic radical, wherein $R^3$ and $R^4$ are independently selected from substituted $C_1$-$C_{18}$ aliphatic radical or substituted $C_4$-$C_{18}$ aromatic radical.

According to an embodiment, the present disclosure relates to compounds of Formula I, its stereoisomers, prodrugs, or pharmaceutically acceptable salts, its stereoisomers, prodrugs, or pharmaceutically acceptable salts thereof:
wherein $R^1$ and $R^2$ are independently selected from substituted or unsubstituted $C_1$-$C_{18}$ aliphatic radical, or substituted or unsubstituted $C_4$-$C_{18}$ aromatic radical;
L is selected from substituted or unsubstituted $C_1$-$C_{18}$ aliphatic radical or substituted or unsubstituted $C_4$-$C_{18}$ aromatic radical; and
Y is selected from $NR^3R^4$ or substituted $C_4$-$C_{18}$ aromatic radical, wherein $R^3$ and $R^4$ are independently selected from substituted $C_1$-$C_{18}$ aliphatic radical or substituted $C_4$-$C_{18}$ aromatic radical.

According to an embodiment, the present disclosure relates to compounds of Formula I, its stereoisomers, prodrugs, or pharmaceutically acceptable salts, its stereoisomers, prodrugs, or pharmaceutically acceptable salts thereof:
wherein $R^1$ and $R^2$ are independently selected from hydrogen;
L is selected from substituted or unsubstituted $C_1$-$C_{18}$ aliphatic radical or substituted or unsubstituted $C_4$-$C_{18}$ aromatic radical; and
Y is selected from $NR^3R^4$ or substituted $C_4$-$C_{18}$ aromatic radical, wherein $R^3$ and $R^4$ are independently selected from substituted $C_1$-$C_{18}$ aliphatic radical or substituted $C_4$-$C_{18}$ aromatic radical.

According to an embodiment, the present disclosure relates to compounds of Formula I, its stereoisomers, prodrugs, or pharmaceutically acceptable salts, its stereoisomers, prodrugs, or pharmaceutically acceptable salts thereof:
wherein $R^1$ and $R^2$ are independently selected from hydrogen;
L is selected from substituted or unsubstituted $C_1$-$C_{18}$ aliphatic radical; and Y is selected from $NR^3R^4$ or substituted $C_4$-$C_{18}$ aromatic radical, wherein $R^3$ and $R^4$ are independently selected from substituted $C_1$-$C_{18}$ aliphatic radical or substituted $C_4$-$C_{18}$ aromatic radical.

According to an embodiment, the present disclosure relates to compounds of Formula I, its stereoisomers, prodrugs, or pharmaceutically acceptable salts, its stereoisomers, prodrugs, or pharmaceutically acceptable salts thereof:
wherein $R^1$ and $R^2$ are independently selected from hydrogen;
L is selected from unsubstituted $C_1$-$C_{18}$ aliphatic radical; and
Y is selected from $NR^3R^4$ or substituted $C_4$-$C_{18}$ aromatic radical, wherein $R^3$ and $R^4$ are independently selected from substituted $C_1$-$C_{18}$ aliphatic radical or substituted $C_4$-$C_{18}$ aromatic radical.

According to an embodiment, the present disclosure relates to compounds of Formula I, its stereoisomers, prodrugs, or pharmaceutically acceptable salts, its stereoisomers, prodrugs, or pharmaceutically acceptable salts thereof:
wherein $R^1$ and $R^2$ are independently selected from hydrogen;
L is selected from unsubstituted $C_1$-$C_{18}$ aliphatic radical; and
Y is selected from $NR^3R^4$, wherein $R^3$ and $R^4$ are independently selected from substituted $C_1$-$C_{18}$ aliphatic radical or substituted $C_4$-$C_{18}$ aromatic radical.

According to an embodiment, the present disclosure relates to compounds of Formula I, its stereoisomers, prodrugs, or pharmaceutically acceptable salts, its stereoisomers, prodrugs, or pharmaceutically acceptable salts thereof:
wherein $R^1$ and $R^2$ are independently selected from hydrogen;
L is selected from unsubstituted $C_1$-$C_{18}$ aliphatic radical; and
Y is substituted $C_4$-$C_{18}$ aromatic radical.

According to an embodiment, the present disclosure relates to compounds of Formula I, its stereoisomers, prodrugs, or pharmaceutically acceptable salts, its stereoisomers, prodrugs, or pharmaceutically acceptable salts thereof:
wherein $R^1$ and $R^2$ are independently selected from hydrogen;
L is selected from unsubstituted $C_1$-$C_{18}$ aliphatic radical; and
Y is selected from $NR^3R^4$, wherein $R^3$ and $R^4$ are independently selected from substituted $C_1$-$C_{18}$ aliphatic radical.

According to an embodiment, the present disclosure relates to compounds of Formula I, its stereoisomers, prodrugs, or pharmaceutically acceptable salts, its stereoisomers, prodrugs, or pharmaceutically acceptable salts thereof:
wherein $R^1$ and $R^2$ are independently selected from hydrogen;
L is selected from unsubstituted $C_1$-$C_{18}$ aliphatic radical; and
Y is selected from $NR^3R^4$, wherein $R^3$ and $R^4$ are independently selected from $C_1$-$C_{18}$ aliphatic radical substituted with $C_6$-$C_{10}$ aryl or $C_5$-$C_{10}$ heteroaryl.

According to an embodiment, the present disclosure relates to compounds of Formula I, its stereoisomers, prodrugs, or pharmaceutically acceptable salts, its stereoisomers, prodrugs, or pharmaceutically acceptable salts thereof:

wherein $R^1$ and $R^2$ are independently selected from hydrogen;
L is selected from unsubstituted $C_3$-$C_8$ aliphatic radical; and
Y is selected from $NR^3R^4$, wherein $R^3$ and $R^4$ are independently selected from $C_1$-$C_4$ aliphatic radical substituted with $C_5$-$C_{10}$ heteroaryl.

According to an embodiment, the present disclosure relates to compounds of Formula I, its stereoisomers, prodrugs, or pharmaceutically acceptable salts, its stereoisomers, prodrugs, or pharmaceutically acceptable salts thereof:
wherein $R^1$ and $R^2$ are independently selected from hydrogen;
L is selected from substituted or unsubstituted $C_4$-$C_{18}$ aromatic radical; and
Y is selected from $NR^3R^4$, wherein $R^3$ and $R^4$ are independently selected from $C_1$-$C_4$ aliphatic radical substituted with $C_5$-$C_{10}$ heteroaryl.

According to an embodiment, the present disclosure relates to compounds of Formula I, its stereoisomers, prodrugs, or pharmaceutically acceptable salts, its stereoisomers, prodrugs, or pharmaceutically acceptable salts thereof:
wherein $R^1$ and $R^2$ are independently selected from hydrogen, substituted or unsubstituted $C_1$-$C_{18}$ aliphatic radical, or substituted or unsubstituted $C_4$-$C_{18}$ aromatic radical;
L is selected from substituted or unsubstituted $C_6$ aliphatic radical; and
Y is selected from $NR^3R^4$ or substituted $C_4$-$C_{18}$ aromatic radical, wherein $R^3$ and $R^4$ are independently selected from substituted $C_1$-$C_{18}$ aliphatic radical or substituted $C_4$-$C_{18}$ aromatic radical.

According to an embodiment, the present disclosure relates to compounds of Formula I, its stereoisomers, prodrugs, or pharmaceutically acceptable salts, its stereoisomers, prodrugs, or pharmaceutically acceptable salts thereof:
wherein $R^1$ and $R^2$ are independently selected from hydrogen, substituted or unsubstituted $C_1$-$C_{18}$ aliphatic radical;
L is selected from substituted or unsubstituted $C_1$-$C_{18}$ aliphatic radical; and
Y is selected from $NR^3R^4$ or substituted $C_4$-$C_{18}$ aromatic radical, wherein $R^3$ and $R^4$ are independently selected from substituted $C_1$-$C_{18}$ aliphatic radical or substituted $C_4$-$C_{18}$ aromatic radical.

According to an embodiment, the present disclosure relates to compounds of Formula I, its stereoisomers, prodrugs, or pharmaceutically acceptable salts, its stereoisomers, prodrugs, or pharmaceutically acceptable salts thereof:
wherein $R^1$ and $R^2$ are independently selected from hydrogen, or substituted or unsubstituted $C_4$-$C_{18}$ aromatic radical;
L is selected from unsubstituted $C_1$-$C_{18}$ aliphatic radical; and
Y is selected from $NR^3R^4$ or substituted $C_4$-$C_{18}$ aromatic radical, wherein $R^3$ and $R^4$ are independently selected from substituted $C_1$-$C_{18}$ aliphatic radical or substituted $C_4$-$C_{18}$ aromatic radical.

According to an embodiment, the present disclosure relates to compounds of Formula I, its stereoisomers, prodrugs, or pharmaceutically acceptable salts, its stereoisomers, prodrugs, or pharmaceutically acceptable salts thereof:
wherein $R^1$ and $R^2$ are independently selected from substituted or unsubstituted $C_1$-$C_{18}$ aliphatic radical, or substituted or unsubstituted $C_4$-$C_{18}$ aromatic radical;

L is selected from unsubstituted $C_1$-$C_{18}$ aliphatic radical; and
Y is selected from $NR^3R^4$, wherein $R^3$ and $R^4$ are independently selected from substituted $C_1$-$C_{18}$ aliphatic radical or substituted $C_4$-$C_{18}$ aromatic radical.

According to an embodiment, the present disclosure relates to compounds of Formula I, its stereoisomers, prodrugs, or pharmaceutically acceptable salts, its stereoisomers, prodrugs, or pharmaceutically acceptable salts thereof:
wherein $R^1$ and $R^2$ are independently selected from hydrogen, substituted or unsubstituted $C_1$-$C_{18}$ aliphatic radical, or substituted or unsubstituted $C_4$-$C_{18}$ aromatic radical;
L is selected from unsubstituted $C_1$-$C_{18}$ aliphatic radical; and
Y is substituted $C_4$-$C_{18}$ aromatic radical.

According to an embodiment, the present disclosure relates to compounds of Formula I, its stereoisomers, prodrugs, or pharmaceutically acceptable salts, its stereoisomers, prodrugs, or pharmaceutically acceptable salts thereof:
wherein $R^1$ and $R^2$ are independently selected from hydrogen, or substituted or unsubstituted $C_4$-$C_{18}$ aromatic radical;
L is selected from unsubstituted $C_1$-$C_{18}$ aliphatic radical; and
Y is selected from $NR^3R^4$, wherein $R^3$ and $R^4$ are independently selected from substituted $C_1$-$C_{18}$ aliphatic radical.

According to an embodiment, the present disclosure relates to compounds of Formula I, its stereoisomers, prodrugs, or pharmaceutically acceptable salts, its stereoisomers, prodrugs, or pharmaceutically acceptable salts thereof:
wherein $R^1$ and $R^2$ are independently selected from substituted or unsubstituted $C_1$-$C_{18}$ aliphatic radical;
L is selected from unsubstituted $C_1$-$C_{18}$ aliphatic radical; and
Y is selected from $NR^3R^4$, wherein $R^3$ and $R^4$ are independently selected from $C_1$-$C_{18}$ aliphatic radical substituted with $C_6$-$C_{10}$ aryl or $C_5$-$C_{10}$ heteroaryl.

According to an embodiment, the present disclosure relates to compounds of Formula I, its stereoisomers, prodrugs, or pharmaceutically acceptable salts, its stereoisomers, prodrugs, or pharmaceutically acceptable salts thereof:
wherein $R^1$ and $R^2$ are independently selected from substituted or unsubstituted $C_4$-$C_{18}$ aromatic radical;
L is selected from unsubstituted $C_3$-$C_8$ aliphatic radical; and
Y is selected from $NR^3R^4$, wherein $R^3$ and $R^4$ are independently selected from $C_1$-$C_4$ aliphatic radical substituted with $C_5$-$C_{10}$ heteroaryl.

According to an embodiment, the present disclosure relates to compounds of Formula I, its stereoisomers, prodrugs, or pharmaceutically acceptable salts, its stereoisomers, prodrugs, or pharmaceutically acceptable salts thereof:
wherein $R^1$ and $R^2$ are independently selected from substituted or unsubstituted $C_4$-$C_{18}$ aromatic radical;
L is selected from substituted or unsubstituted $C_4$-$C_{18}$ aromatic radical; and
Y is selected from $NR^3R^4$, wherein $R^3$ and $R^4$ are independently selected from $C_1$-$C_4$ aliphatic radical substituted with $C_5$-$C_{10}$ heteroaryl.

According to an embodiment, the present disclosure relates to compounds of Formula I, its stereoisomers, prodrugs, or pharmaceutically acceptable salts, its stereoisomers, prodrugs, or pharmaceutically acceptable salts thereof:

wherein $R^1$ and $R^2$ are independently selected from hydrogen, substituted or unsubstituted $C_2$-$C_{18}$ aliphatic radical or substituted or unsubstituted $C_4$-$C_{18}$ aromatic radical;
L is selected from substituted or unsubstituted $C_2$-$C_{12}$ aliphatic radical;
Y is selected from $NR^3R^4$ or substituted $C_4$-$C_{18}$ aromatic radical, wherein $R^3$ and $R^4$ are independently selected from H, substituted $C_1$-$C_{10}$ aliphatic radical or substituted $C_4$-$C_{18}$ aromatic radical.

According to an embodiment, the present disclosure relates to compounds of Formula I, its stereoisomers, prodrugs, or pharmaceutically acceptable salts, its stereoisomers, prodrugs, or pharmaceutically acceptable salts thereof:
wherein $R^1$ and $R^2$ are independently selected from hydrogen, substituted or unsubstituted $C_2$-$C_{18}$ aliphatic radical or substituted or unsubstituted $C_4$-$C_{18}$ aromatic radical;
L is selected from substituted or unsubstituted $C_2$-$C_{10}$ aliphatic radical;
Y is selected from $NR^3R^4$, wherein $R^3$ and $R^4$ are independently selected from H, substituted $C_1$-$C_{10}$ aliphatic radical or substituted $C_4$-$C_{18}$ aromatic radical.

According to an embodiment, the present disclosure relates to compounds of Formula I, its stereoisomers, prodrugs, or pharmaceutically acceptable salts, its stereoisomers, prodrugs, or pharmaceutically acceptable salts thereof:
wherein $R^1$ and $R^2$ are independently selected from hydrogen, substituted or unsubstituted $C_2$-$C_{18}$ aliphatic radical, or substituted or unsubstituted $C_4$-$C_{18}$ aromatic radical;
L is selected from substituted or unsubstituted $C_4$-$C_8$ aliphatic radical;
Y is selected from $NR^3R^4$, wherein $R^3$ and $R^4$ are independently selected $C_1$-$C_6$ aliphatic radical substituted with $C_4$-$C_{18}$ heteroaryl, wherein $C_4$-$C_{18}$ heteroaryl is optionally substituted with up to four substituents selected from halogen, substituted or unsubstituted $C_1$-$C_{18}$ aliphatic radical or substituted or unsubstituted $C_4$-$C_{18}$ aromatic radical According to an embodiment, the present disclosure relates to compounds of Formula I, its stereoisomers, prodrugs, or pharmaceutically acceptable salts, its stereoisomers, prodrugs, or pharmaceutically acceptable salts thereof:
wherein $R^1$ and $R^2$ are independently selected from hydrogen, unsubstituted $C_2$-$C_{10}$ aliphatic radical or substituted or unsubstituted $C_4$-$C_{10}$ aromatic radical;
L is selected from substituted or unsubstituted $C_6$ aliphatic radical;
Y is selected from $NR^3R^4$, wherein $R^3$ and $R^4$ are independently selected from $C_1$-$C_3$ aliphatic radical substituted with $C_5$ heteroaryl.

One embodiment of the present disclosure is a compound of Formula I, its stereoisomers, prodrugs, or pharmaceutically acceptable salts, its stereoisomers, prodrugs, or pharmaceutically acceptable salts thereof, selected from, An embodiment of the present disclosure also relates to a compound of Formula I, its stereoisomers, prodrugs, or pharmaceutically acceptable salts, its stereoisomers, prodrugs, or pharmaceutically acceptable salts thereof, for use as a medicament.

Another embodiment of the present disclosure also relates to a compound of Formula I, its stereoisomers, prodrugs, or pharmaceutically acceptable salts, its stereoisomers, prodrugs, or pharmaceutically acceptable salts thereof, for use in treatment of a bacterial infection.

Another embodiment of the present disclosure also relates to a compound of Formula I, its stereoisomers, prodrugs, or pharmaceutically acceptable salts, its stereoisomers, prodrugs, or pharmaceutically acceptable salts thereof, for use in treatment of a bacterial infection caused by *Mycobacterium tuberculosis*.

Yet another embodiment of the present disclosure also relates to a compound of Formula I, its stereoisomers, prodrugs, or pharmaceutically acceptable salts, its stereoisomers, prodrugs, or pharmaceutically acceptable salts thereof, for use in the treatment of diseases caused by gram positive bacteria.

Yet another embodiment of the present disclosure also relates to a compound of Formula I, its stereoisomers, prodrugs, or pharmaceutically acceptable salts thereof, for use in the treatment of diseases caused by gram negative bacteria.

Yet another embodiment of the present disclosure also relates to a compound of Formula I, its stereoisomers, prodrugs, or pharmaceutically acceptable salts thereof for use in treatment of a bacterial infection, wherein the bacterium comprises a vancomycin-resistant bacterium, a methicillin-resistant bacterium, or carbapenem-resistant bacterium.

Yet another embodiment of the present disclosure also relates to a compound of Formula I or its stereoisomers, prodrugs and the pharmaceutically acceptable salts thereof for use in treatment of a bacterial infection, wherein the bacterium comprises a vancomycin-resistant *Staphylococcus aureus*, a vancomycin-resistant *Enterococcus faecium*, a vancomycin-resistant *Enterococcus faecalis*, a methicillin-resistant *Staphylococcus aureus*, or a meropenem-resistant NDM-1 gene expressing gram negative pathogens.

Yet another embodiment of the present disclosure also relates to a method for treatment of bacterial infection in a subject comprising: administering to the subject an effective amount of the compound of Formula I, its stereoisomers, prodrugs, or pharmaceutically acceptable salts thereof. The subject can be any living organism, particularly animal or human, preferably human.

Yet another embodiment of the present disclosure also relates to a method for treatment of bacterial infection in a subject caused by a gram-positive bacterium comprising: administering to the subject an effective amount of the compound of Formula I, its stereoisomers, prodrugs, or pharmaceutically acceptable salts thereof.

Yet another embodiment of the present disclosure also relates to a method for treatment of bacterial infection in a subject caused by a gram-negative bacterium comprising: administering to the subject an effective amount of the compound of Formula I, its stereoisomers, prodrugs, or pharmaceutically acceptable salts thereof.

Yet another embodiment of the present disclosure also relates to a method for treatment of bacterial infection in a subject caused by a drug-resistant bacterium comprising: administering to the subject an effective amount of the compound of Formula I, its stereoisomers, prodrugs, or pharmaceutically acceptable salts thereof.

Yet another embodiment of the present disclosure also relates to a method for treatment of bacterial infection in a subject caused by a vancomycin-resistant bacterium comprising: administering to the subject an effective amount of the compound of Formula I, its stereoisomers, prodrugs, or pharmaceutically acceptable salts thereof.

Yet another embodiment of the present disclosure also relates to a method for treatment of bacterial infection in a subject caused by a methicillin-resistant bacterium comprising: administering to the subject an effective amount of the compound of Formula I, its stereoisomers, prodrugs, or pharmaceutically acceptable salts thereof.

Yet another embodiment of the present disclosure also relates to a method for treatment of bacterial infection in a subject caused by a carbapenem-resistant bacterium comprising: administering to the subject an effective amount of the compound of Formula I, its stereoisomers, prodrugs, or pharmaceutically acceptable salts thereof.

Yet another embodiment of the present disclosure also relates to a method for treatment of bacterial infection in a subject caused by a drug-resistant bacterium, wherein the bacterium comprises a vancomycin-resistant *Staphylococcus aureus*, a vancomycin-resistant *Enterococcus faecium*, a vancomycin-resistant *Enterococcus faecalis*, or a methicillin-resistant *Staphylococcus aureus* or a meropenem-resistant NDM-1 gene expressing gram negative pathogens, comprising: administering to the subject an effective amount of the compound of Formula I, its stereoisomers, prodrugs, or pharmaceutically acceptable salts thereof.

Another embodiment of the present disclosure relates to a process of preparing the compounds of Formula I, its stereoisomers, prodrugs, or pharmaceutically acceptable salts thereof.

Another embodiment of the present disclosure relates to a pharmaceutical composition comprising a compound of Formula I or its pharmaceutically acceptable salts thereof, together with a pharmaceutically acceptable carrier and a method of preparing the same.

Yet another embodiment of the present disclosure relates to a pharmaceutical composition comprising a therapeutically effective amount of a compound of the present disclosure, alone or in combination with one or more pharmaceutically acceptable carriers.

The present disclosure provides a metal coordination complex of a compound of Formula I its stereoisomers, prodrugs, or pharmaceutically acceptable salts thereof, and a metal:

wherein $R^1$ and $R^2$ are independently selected from hydrogen, substituted or unsubstituted $C_1$-$C_{18}$ aliphatic radical or substituted or unsubstituted $C_4$-$C_{18}$ aromatic radical;

L is selected from substituted or unsubstituted $C_1$-$C_{18}$ aliphatic radical or substituted or unsubstituted $C_4$-$C_{18}$ aromatic radical;

Y is selected from $NR^3R^4$ or substituted $C_4$-$C_{18}$ aromatic radical, wherein $R^3$ and $R^4$ are independently selected from substituted $C_1$-$C_{18}$ aliphatic radical or substituted $C_4$-$C_{18}$ aromatic radical; and the metal is a transitional metal.

According to an embodiment, the present disclosure relates to a metal coordination complex of a compound of Formula I, its stereoisomers, prodrugs, or pharmaceutically acceptable salts thereof, and a metal:

wherein $R^1$ and $R^2$ are independently selected from hydrogen, or substituted or unsubstituted $C_1$-$C_{18}$ aliphatic radical;

L is selected from substituted or unsubstituted $C_1$-$C_{18}$ aliphatic radical or substituted or unsubstituted $C_4$-$C_{18}$ aromatic radical;

Y is selected from $NR^3R^4$ or substituted $C_4$-$C_{18}$ aromatic radical, wherein $R^3$ and $R^4$ are independently selected from substituted $C_1$-$C_{18}$ aliphatic radical or substituted $C_4$-$C_{18}$ aromatic radical; and the metal is a transitional metal.

According to an embodiment, the present disclosure relates to a metal coordination complex of a compound of Formula I, its stereoisomers, prodrugs, or pharmaceutically acceptable salts thereof, and a metal:

wherein $R^1$ and $R^2$ are independently selected from hydrogen, or substituted or unsubstituted $C_4$-$C_{18}$ aromatic radical;

L is selected from substituted or unsubstituted $C_1$-$C_{18}$ aliphatic radical or substituted or unsubstituted $C_4$-$C_{18}$ aromatic radical;

Y is selected from $NR^3R^4$ or substituted $C_4$-$C_{18}$ aromatic radical, wherein $R^3$ and $R^4$ are independently selected from substituted $C_1$-$C_{18}$ aliphatic radical or substituted $C_4$-$C_{18}$ aromatic radical; and Formula I

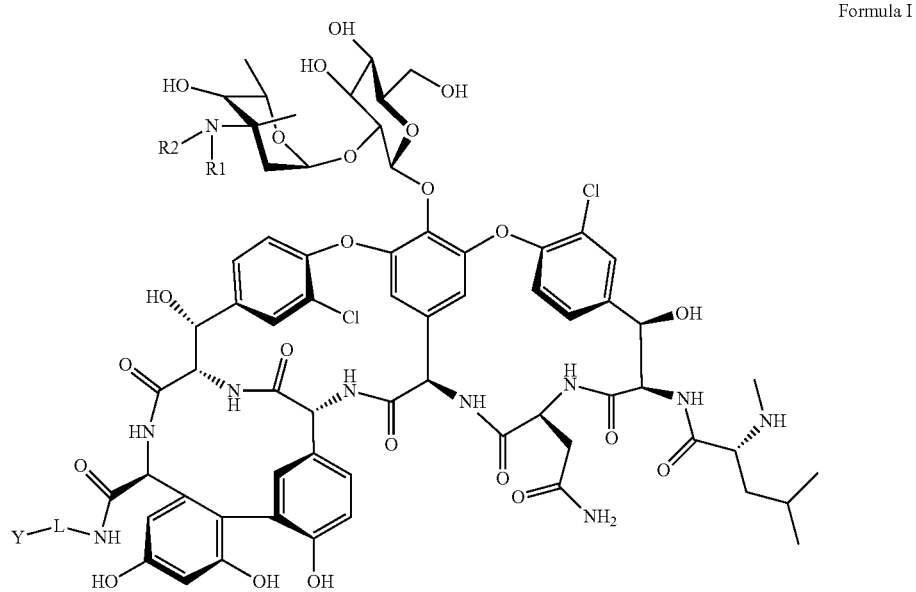

the metal is a transitional metal

According to an embodiment, the present disclosure relates to a metal coordination complex of a compound of Formula I, its stereoisomers, prodrugs, or pharmaceutically acceptable salts thereof, and a metal:

wherein $R^1$ and $R^2$ are independently selected from substituted or unsubstituted $C_1$-$C_{18}$ aliphatic radical, or substituted or unsubstituted $C_4$-$C_{18}$ aromatic radical;
L is selected from substituted or unsubstituted $C_1$-$C_{18}$ aliphatic radical or substituted or unsubstituted $C_4$-$C_{18}$ aromatic radical;
Y is selected from $NR^3R^4$ or substituted $C_4$-$C_{18}$ aromatic radical, wherein $R^3$ and $R^4$ are independently selected from substituted $C_1$-$C_{18}$ aliphatic radical or substituted $C_4$-$C_{18}$ aromatic radical; and
the metal is a transitional metal.

According to an embodiment, the present disclosure relates to a metal coordination complex of a compound of Formula I, its stereoisomers, prodrugs, or pharmaceutically acceptable salts thereof, and a metal:
wherein $R^1$ and $R^2$ are independently selected from hydrogen;
L is selected from substituted or unsubstituted $C_1$-$C_{18}$ aliphatic radical or substituted or unsubstituted $C_4$-$C_{18}$ aromatic radical;
Y is selected from $NR^3R^4$ or substituted $C_4$-$C_{18}$ aromatic radical, wherein $R^3$ and $R^4$ are independently selected from substituted $C_1$-$C_{18}$ aliphatic radical or substituted $C_4$-$C_{18}$ aromatic radical; and
the metal is a transitional metal.

According to an embodiment, the present disclosure relates to a metal coordination complex of a compound of Formula I, its stereoisomers, prodrugs, or pharmaceutically acceptable salts thereof, and a metal:
wherein $R^1$ and $R^2$ are independently selected from hydrogen;
L is selected from substituted or unsubstituted $C_1$-$C_{18}$ aliphatic radical;
Y is selected from $NR^3R^4$ or substituted $C_4$-$C_{18}$ aromatic radical, wherein $R^3$ and $R^4$ are independently selected from substituted $C_1$-$C_{18}$ aliphatic radical or substituted $C_4$-$C_{18}$ aromatic radical; and
the metal is a transitional metal.

According to an embodiment, the present disclosure relates to a metal coordination complex of a compound of Formula I, its stereoisomers, prodrugs, or pharmaceutically acceptable salts thereof, and a metal:
wherein $R^1$ and $R^2$ are independently selected from hydrogen;
L is selected from unsubstituted $C_1$-$C_{18}$ aliphatic radical;
Y is selected from $NR^3R^4$ or substituted $C_4$-$C_{18}$ aromatic radical, wherein $R^3$ and $R^4$ are independently selected from substituted $C_1$-$C_{18}$ aliphatic radical or substituted $C_4$-$C_{18}$ aromatic radical; and
the metal is a transitional metal.

According to an embodiment, the present disclosure relates to a metal coordination complex of a compound of Formula I, its stereoisomers, prodrugs, or pharmaceutically acceptable salts thereof, and a metal:
wherein $R^1$ and $R^2$ are independently selected from hydrogen;

L is selected from unsubstituted $C_1$-$C_{18}$ aliphatic radical;
Y is substituted $C_4$-$C_{18}$ aromatic radical; and
the metal is a transitional metal.

According to an embodiment, the present disclosure relates to a metal coordination complex of a compound of Formula I, its stereoisomers, prodrugs, or pharmaceutically acceptable salts thereof, and a metal:
wherein $R^1$ and $R^2$ are independently selected from hydrogen;
L is selected from unsubstituted $C_1$-$C_{18}$ aliphatic radical;
Y is selected from $NR^3R^4$, wherein $R^3$ and $R^4$ are independently selected from substituted $C_1$-$C_{18}$ aliphatic radical; and
the metal is a transitional metal.

According to an embodiment, the present disclosure relates to a metal coordination complex of a compound of Formula I, its stereoisomers, prodrugs, or pharmaceutically acceptable salts thereof, and a metal:
wherein $R^1$ and $R^2$ are independently selected from hydrogen;
L is selected from unsubstituted $C_1$-$C_{18}$ aliphatic radical;
Y is selected from $NR^3R^4$, wherein $R^3$ and $R^4$ are independently selected from $C_1$-$C_{18}$ aliphatic radical substituted with $C_6$-$C_{10}$ aryl or $C_5$-$C_{10}$ heteroaryl; and
the metal is a transitional metal.

According to an embodiment, the present disclosure relates to a metal coordination complex of a compound of Formula I, its stereoisomers, prodrugs, or pharmaceutically acceptable salts thereof, and a metal:
wherein $R^1$ and $R^2$ are independently selected from hydrogen;
L is selected from unsubstituted $C_3$-$C_5$ aliphatic radical;
Y is selected from $NR^3R^4$, wherein $R^3$ and $R^4$ are independently selected from $C_1$-$C_4$ aliphatic radical substituted with $C_5$-$C_{10}$ heteroaryl; and
the metal is a transitional metal.

According to an embodiment, the present disclosure relates to a metal coordination complex of a compound of Formula I, its stereoisomers, prodrugs, or pharmaceutically acceptable salts thereof, and a metal:
wherein $R^1$ and $R^2$ are independently selected from hydrogen;
L is selected from substituted or unsubstituted $C_4$-$C_{18}$ aromatic radical;
Y is selected from $NR^3R^4$, wherein $R^3$ and $R^4$ are independently selected from $C_1$-$C_4$ aliphatic radical substituted with $C_5$-$C_{10}$ heteroaryl; and
the metal is a transitional metal.

According to an embodiment, the present disclosure relates to a metal coordination complex of a compound of Formula I, its stereoisomers, prodrugs, or pharmaceutically acceptable salts thereof, and a metal:
wherein $R^1$ and $R^2$ are independently selected from hydrogen, substituted or unsubstituted $C_1$-$C_{18}$ aliphatic radical, or substituted or unsubstituted $C_4$-$C_{18}$ aromatic radical;
L is selected from substituted or unsubstituted $C_1$-$C_{18}$ aliphatic radical or substituted or unsubstituted $C_4$-$C_{18}$ aromatic radical;
Y is selected from $NR^3R^4$ or substituted $C_4$-$C_{18}$ aromatic radical, wherein $R^3$ and $R^4$ are independently selected from substituted $C_1$-$C_{18}$ aliphatic radical or substituted $C_4$-$C_{18}$ aromatic radical; and
the metal is a transitional metal selected from the group consisting of manganese, titanium, cobalt, copper, vanadium, nickel, tungsten, molybdenum, chromium, zinc, and combinations thereof.

According to an embodiment, the present disclosure relates to a metal coordination complex of a compound of Formula I, its stereoisomers, prodrugs, or pharmaceutically acceptable salts thereof, and a metal:
wherein $R^1$ and $R^2$ are independently selected from hydrogen, or substituted or unsubstituted $C_1$-$C_{18}$ aliphatic radical;
L is selected from substituted or unsubstituted $C_1$-$C_{18}$ aliphatic radical;
Y is selected from $NR^3R^4$ or substituted $C_4$-$C_{18}$ aromatic radical, wherein $R^3$ and $R^4$ are independently selected from substituted $C_1$-$C_{18}$ aliphatic radical or substituted $C_4$-$C_{18}$ aromatic radical; and
the metal is a transitional metal.

According to an embodiment, the present disclosure relates to a metal coordination complex of a compound of Formula I, its stereoisomers, prodrugs, or pharmaceutically acceptable salts thereof, and a metal:
wherein $R^1$ and $R^2$ are independently selected from hydrogen, or substituted or unsubstituted $C_4$-$C_{18}$ aromatic radical;
L is selected from unsubstituted $C_1$-$C_{18}$ aliphatic radical;
Y is selected from $NR^3R^4$ or substituted $C_4$-$C_{18}$ aromatic radical, wherein $R^3$ and $R^4$ are independently selected from substituted $C_1$-$C_{18}$ aliphatic radical or substituted $C_4$-$C_{18}$ aromatic radical; and
the metal is a transitional metal.

According to an embodiment, the present disclosure relates to a metal coordination complex of a compound of Formula I, its stereoisomers, prodrugs, or pharmaceutically acceptable salts thereof, and a metal:
wherein $R^1$ and $R^2$ are independently selected from substituted or unsubstituted $C_1$-$C_{18}$ aliphatic radical, or substituted or unsubstituted $C_4$-$C_{18}$ aromatic radical;
L is selected from unsubstituted $C_1$-$C_{18}$ aliphatic radical;
Y is selected from $NR^3R^4$, wherein $R^3$ and $R^4$ are independently selected from substituted $C_1$-$C_{18}$ aliphatic radical or substituted $C_4$-$C_{18}$ aromatic radical; and
the metal is a transitional metal.

According to an embodiment, the present disclosure relates to a metal coordination complex of a compound of Formula I, its stereoisomers, prodrugs, or pharmaceutically acceptable salts thereof, and a metal:
wherein $R^1$ and $R^2$ are independently selected from hydrogen, substituted or unsubstituted $C_1$-$C_{18}$ aliphatic radical, or substituted or unsubstituted $C_4$-$C_{18}$ aromatic radical;
L is selected from unsubstituted $C_1$-$C_{18}$ aliphatic radical;
Y is substituted $C_4$-$C_{18}$ aromatic radical; and
the metal is a transitional metal.

According to an embodiment, the present disclosure relates to a metal coordination complex of a compound of Formula I, its stereoisomers, prodrugs, or pharmaceutically acceptable salts thereof, and a metal:
wherein $R^1$ and $R^2$ are independently selected from hydrogen, or substituted or unsubstituted $C_4$-$C_{18}$ aromatic radical;
L is selected from unsubstituted $C_1$-$C_{18}$ aliphatic radical;
Y is selected from $NR^3R^4$, wherein $R^3$ and $R^4$ are independently selected from substituted $C_1$-$C_{18}$ aliphatic radical; and
the metal is a transitional metal.

According to an embodiment, the present disclosure relates to a metal coordination complex of a compound of Formula I, its stereoisomers, prodrugs, or pharmaceutically acceptable salts thereof, and a metal:
wherein $R^1$ and $R^2$ are independently selected from substituted or unsubstituted $C_1$-$C_{18}$ aliphatic radical;
L is selected from unsubstituted $C_1$-$C_{18}$ aliphatic radical;
Y is selected from $NR^3R^4$, wherein $R^3$ and $R^4$ are independently selected from $C_1$-$C_{18}$ aliphatic radical substituted with $C_6$-$C_{10}$ aryl or $C_5$-$C_{10}$ heteroaryl; and
the metal is a transitional metal.

According to an embodiment, the present disclosure relates to a metal coordination complex of a compound of Formula I, its stereoisomers, prodrugs, or pharmaceutically acceptable salts thereof, and a metal:
wherein $R^1$ and $R^2$ are independently selected from substituted or unsubstituted $C_4$-$C_{18}$ aromatic radical;
L is selected from unsubstituted $C_3$-$C_8$ aliphatic radical;
Y is selected from $NR^3R^4$, wherein $R^3$ and $R^4$ are independently selected from $C_1$-$C_4$ aliphatic radical substituted with $C_5$-$C_{10}$ heteroaryl; and
the metal is a transitional metal.

According to an embodiment, the present disclosure relates to a metal coordination complex of a compound of Formula I, its stereoisomers, prodrugs, or pharmaceutically acceptable salts thereof, and a metal:
wherein $R^1$ and $R^2$ are independently selected from substituted or unsubstituted $C_4$-$C_{18}$ aromatic radical;
L is selected from substituted or unsubstituted $C_4$-$C_{18}$ aromatic radical;
Y is selected from $NR^3R^4$, wherein $R^3$ and $R^4$ are independently selected from $C_1$-$C_4$ aliphatic radical substituted with $C_5$-$C_{10}$ heteroaryl; and
the metal is a transitional metal.

According to an embodiment, the present disclosure relates to a metal coordination complex of a compound of Formula I, its stereoisomers, prodrugs, or pharmaceutically acceptable salts thereof, and a metal:
wherein $R^1$ and $R^2$ are independently selected from hydrogen, substituted or unsubstituted $C_2$-$C_{18}$ aliphatic radical or substituted or unsubstituted $C_4$-$C_{18}$ aromatic radical;
L is selected from substituted or unsubstituted $C_2$-$C_{12}$ aliphatic radical;
Y is selected from $NR^3R^4$ or substituted $C_4$-$C_{18}$ aromatic radical, wherein $R^3$ and $R^4$ are independently selected from H, substituted $C_1$-$C_{10}$ aliphatic radical or substituted $C_4$-$C_{18}$ aromatic radical; and
the metal is a transitional metal.

According to an embodiment, the present disclosure relates to a metal coordination complex of a compound of Formula I, its stereoisomers, prodrugs, or pharmaceutically acceptable salts thereof, and a metal:
wherein $R^1$ and $R^2$ are independently selected from hydrogen, substituted or unsubstituted $C_2$-$C_{18}$ aliphatic radical or substituted or unsubstituted $C_4$-$C_{18}$ aromatic radical;
L is selected from substituted or unsubstituted $C_2$-$C_{10}$ aliphatic radical;
Y is selected from $NR^3R^4$, wherein $R^3$ and $R^4$ are independently selected from H, substituted $C_1$-$C_{10}$ aliphatic radical or substituted $C_4$-$C_{18}$ aromatic radical; and
the metal is a transitional metal.

According to an embodiment, the present disclosure relates to a metal coordination complex of a compound of Formula I, its stereoisomers, prodrugs, or pharmaceutically acceptable salts thereof, and a metal:
wherein $R^1$ and $R^2$ are independently selected from hydrogen, substituted or unsubstituted $C_2$-$C_{18}$ aliphatic radical or substituted or unsubstituted $C_4$-$C_{18}$ aromatic radical;
L is selected from substituted or unsubstituted $C_4$-$C_8$ aliphatic radical;
Y is selected from $NR^3R^4$, wherein $R^3$ and $R^4$ are independently selected $C_1$-$C_6$ aliphatic radical substituted with $C_4$-$C_{18}$ heteroaryl, wherein $C_4$-$C_{18}$ heteroaryl is optionally substituted with up to four substituents selected from halogen, substituted or unsubstituted $C_1$-$C_{18}$ aliphatic radical or substituted or unsubstituted $C_4$-$C_{18}$ aromatic radical; and the metal is a transitional metal selected from the group consisting of manganese, titanium, cobalt, copper, vanadium, nickel, tungsten, molybdenum, and chromium, zinc, and combinations thereof.

According to an embodiment, the present disclosure relates to a metal coordination complex of a compound of Formula I, its stereoisomers, prodrugs, or pharmaceutically acceptable salts thereof, and a metal:
wherein $R^1$ and $R^2$ are independently selected from hydrogen, unsubstituted $C_2$-$C_{10}$ aliphatic radical or substituted or unsubstituted $C_4$-$C_{10}$ aromatic radical;

L is selected from substituted or unsubstituted $C_6$ aliphatic radical;

Y is selected from $NR^3R^4$, wherein $R_3$ and $R_4$ are independently selected from $C_1$-$C_3$ aliphatic radical substituted with $C_5$ heteroaryl;

and the metal is zinc.

One embodiment of the present disclosure is a metal coordination complex of a compound of Formula I, its stereoisomers, prodrugs, or pharmaceutically acceptable salts thereof, and a metal, selected from,

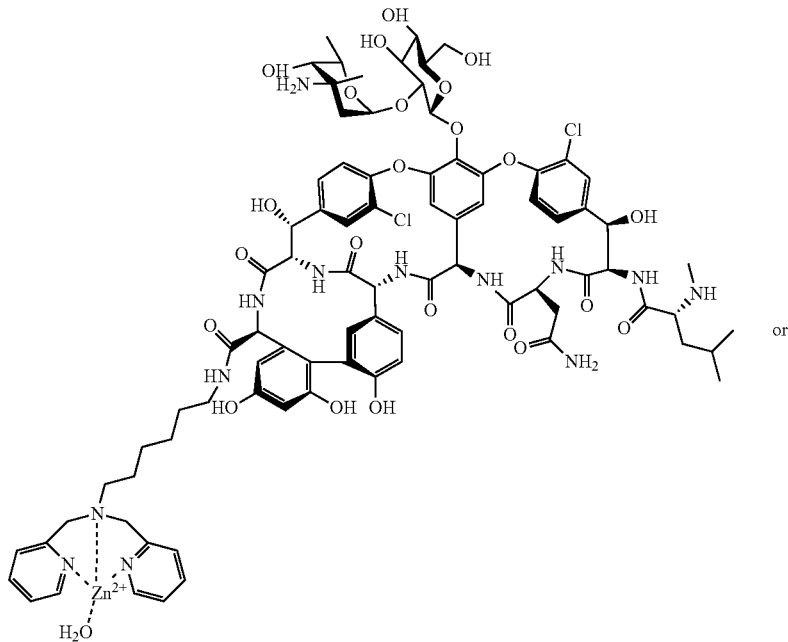

Compound 5 or

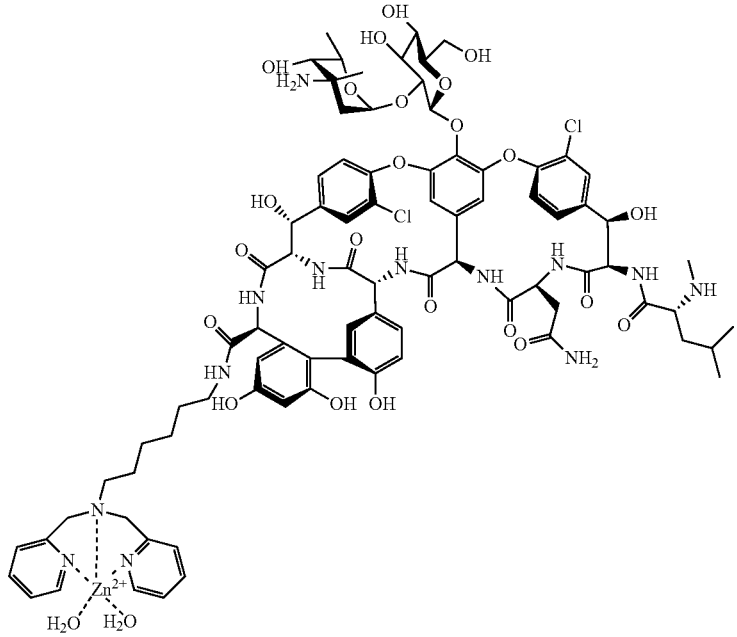

Compound 6

An embodiment of the present disclosure also relates to a metal coordination complex of a compound of Formula I, its stereoisomers, prodrugs, or pharmaceutically acceptable salts thereof, and a metal, for use as a medicament.

Another embodiment of the present disclosure also relates to a metal coordination complex of a compound of Formula I, its stereoisomers, prodrugs, or pharmaceutically acceptable salts thereof, and a metal, for use in treatment of a bacterial infection.

Another embodiment of the present disclosure also relates to a metal coordination complex of a compound of Formula I, its stereoisomers, prodrugs, or pharmaceutically acceptable salts thereof, and a metal, for use in treatment of a bacterial infection caused by *Mycobacterium tuberculosis*.

Yet another embodiment of the present disclosure also relates to a metal coordination complex of a compound of Formula I, its stereoisomers, prodrugs, or pharmaceutically acceptable salts thereof, and a metal, for use in the treatment of diseases caused by gram positive bacteria.

Yet another embodiment of the present disclosure also relates to a metal coordination complex of a compound of Formula I, its stereoisomers, prodrugs, or pharmaceutically acceptable salts thereof, and a metal, for use in the treatment of diseases caused by gram negative bacteria.

Yet another embodiment of the present disclosure also relates to a metal coordination complex of a compound of Formula I, its stereoisomers, prodrugs, or pharmaceutically acceptable salts thereof, and a metal for use in treatment of a bacterial infection, wherein the bacterium comprises a vancomycin-resistant bacterium, a methicillin-resistant bacterium, or carbapenem-resistant bacterium.

Yet another embodiment of the present disclosure also relates to a metal coordination complex of a compound of Formula I, its stereoisomers, prodrugs, or pharmaceutically acceptable salts thereof, and a metal for use in treatment of a bacterial infection, wherein the bacterium comprises a vancomycin-resistant *Staphylococcus aureus*, a vancomycin-resistant *Enterococcus faecium*, a methicillin-resistant *Staphylococcus aureus*, or a meropenem-resistant NDM-1 gene expressing gram negative pathogens.

Yet another embodiment of the present disclosure also relates to a method for treatment of bacterial infection in a subject comprising: administering to the subject an effective amount of the metal coordination complex of a compound of Formula I, its stereoisomers, prodrugs, or pharmaceutically acceptable salts thereof, and a metal.

Yet another embodiment of the present disclosure also relates to a method for treatment of bacterial infection in a subject caused by a gram-positive bacterium comprising: administering to the subject an effective amount of the metal coordination complex of a compound of Formula I, its stereoisomers, prodrugs, or pharmaceutically acceptable salts thereof, and a metal.

Yet another embodiment of the present disclosure also relates to a method for treatment of bacterial infection in a subject caused by a gram-negative bacterium comprising: administering to the subject an effective amount of the metal coordination complex of a compound of Formula I, its stereoisomers, prodrugs, or pharmaceutically acceptable salts thereof, and a metal.

Yet another embodiment of the present disclosure also relates to a method for treatment of bacterial infection in a subject caused by a drug-resistant bacterium comprising: administering to the subject an effective amount of the metal coordination complex of a compound of Formula I, its stereoisomers, prodrugs, or pharmaceutically acceptable salts thereof, and a metal.

Yet another embodiment of the present disclosure also relates to a method for treatment of bacterial infection in a subject caused by a vancomycin-resistant bacterium comprising: administering to the subject an effective amount of the metal coordination complex of a compound of Formula I, its stereoisomers, prodrugs, or pharmaceutically acceptable salts thereof, and a metal.

Yet another embodiment of the present disclosure also relates to a method for treatment of bacterial infection in a subject caused by a methicillin-resistant bacterium comprising: administering to the subject an effective amount of the metal coordination complex of a compound of Formula I, its stereoisomers, prodrugs, or pharmaceutically acceptable salts thereof, and a metal.

Yet another embodiment of the present disclosure also relates to a method for treatment of bacterial infection in a subject caused by a carbapenem-resistant bacterium comprising: administering to the subject an effective amount of the metal coordination complex of a compound of Formula I, its stereoisomers, prodrugs, or pharmaceutically acceptable salts thereof, and a metal.

Yet another embodiment of the present disclosure also relates to a method for treatment of bacterial infection in a subject caused by a drug-resistant bacterium, wherein the bacterium comprises a vancomycin-resistant *Staphylococcus aureus*, a vancomycin-resistant *Enterococcus faecium* or a methicillin-resistant *Staphylococcus aureus* or a meropenem-resistant NDM-1 gene expressing gram negative pathogens, comprising: administering to the subject an effective amount of the metal coordination complex of a compound of Formula I, its stereoisomers, prodrugs, or pharmaceutically acceptable salts thereof, and a metal.

Another embodiment of the present disclosure relates to a pharmaceutical composition comprising a metal coordination complex of a compound of Formula I, its stereoisomers, prodrugs, or pharmaceutically acceptable salts thereof, and a metal, together with a pharmaceutically acceptable carrier and a method of preparing the same.

Another embodiment of the present disclosure relates to a method of preparing the metal coordination complexes of a compound of Formula I, its stereoisomers, prodrugs, or pharmaceutically acceptable salts thereof, and a metal.

Yet another embodiment of the present disclosure relates to a pharmaceutical composition comprising a therapeutically effective amount of a metal coordination complex of a compound of Formula I, its stereoisomers, prodrugs, or pharmaceutically acceptable salts thereof, and a metal, alone or in combination with one or more pharmaceutically acceptable carriers.

An embodiment of the present disclosure relates to a pharmaceutical composition comprising a compound of Formula I, its stereoisomers, prodrugs, or pharmaceutically acceptable salts thereof, and an antibiotic and a method of preparing the same.

Another embodiment of the present disclosure relates to a pharmaceutical composition comprising a compound of Formula I, its stereoisomers, prodrugs, or pharmaceutically acceptable salts thereof and β-lactam antibiotic and a method of preparing the same. Examples of β-lactam include penicillins, cephalosporins, carbapenems and monobactams Yet another embodiment of the present disclosure relates to a pharmaceutical composition comprising a compound of Formula I, its stereoisomers, prodrugs, or pharmaceutically acceptable salts thereof and meropenem antibiotic and a method of preparing the same.

Yet another embodiment of the present disclosure relates to a pharmaceutical composition comprising a compound of Formula I, its stereoisomers, prodrugs, or pharmaceutically acceptable salts thereof and carbapenem.

An embodiment of the present disclosure also relates to a pharmaceutical composition comprising a compound of Formula I, its stereoisomers, prodrugs, or pharmaceutically acceptable salts thereof and an antibiotic, for use as a medicament.

Another embodiment of the present disclosure also relates to a pharmaceutical composition comprising a compound of Formula I, its stereoisomers, prodrugs, or pharmaceutically acceptable salts thereof and an antibiotic, for use in treatment of a bacterial infection.

Another embodiment of the present disclosure also relates to a pharmaceutical composition comprising a compound of Formula I, its stereoisomers, prodrugs, or pharmaceutically acceptable salts thereof and an antibiotic, for use in treatment of a bacterial infection caused by *Mycobacterium tuberculosis*.

Yet another embodiment of the present disclosure also relates to a pharmaceutical composition comprising a compound of Formula I, its stereoisomers, prodrugs, or pharmaceutically acceptable salts thereof and an antibiotic, for use in the treatment of diseases caused by gram positive bacteria.

Yet another embodiment of the present disclosure also relates to a pharmaceutical composition comprising a compound of Formula I, its stereoisomers, prodrugs, or pharmaceutically acceptable salts thereof and an antibiotic, for use in the treatment of diseases caused by gram negative bacteria.

Yet another embodiment of the present disclosure also relates to a pharmaceutical composition comprising a compound of Formula I, its stereoisomers, prodrugs, or pharmaceutically acceptable salts thereof and an antibiotic for use in treatment of a bacterial infection, wherein the bacterium comprises a vancomycin-resistant bacterium, a methicillin-resistant bacterium, or carbapenem-resistant bacterium.

Yet another embodiment of the present disclosure also relates to a pharmaceutical composition comprising a compound of Formula I, its stereoisomers, prodrugs, or pharmaceutically acceptable salts thereof and an antibiotic for use in treatment of a bacterial infection, wherein the bacterium comprises a vancomycin-resistant *Staphylococcus aureus*, a vancomycin-resistant *Enterococcus faecium*, a methicillin-resistant *Staphylococcus aureus*, or a meropenem-resistant NDM-1 gene expressing gram negative pathogens.

Yet another embodiment of the present disclosure also relates to a method for treatment of bacterial infection in a subject comprising: administering to the subject an effective amount of a pharmaceutical composition comprising a compound of Formula I, its stereoisomers, prodrugs, or pharmaceutically acceptable salts thereof and an antibiotic.

Yet another embodiment of the present disclosure also relates to a method for treatment of bacterial infection in a subject caused by a gram-positive bacterium comprising: administering to the subject an effective amount of a pharmaceutical composition comprising a compound of Formula I, its stereoisomers, prodrugs, or pharmaceutically acceptable salts thereof and an antibiotic.

Yet another embodiment of the present disclosure also relates to a method for treatment of bacterial infection in a subject caused by a gram-negative bacterium comprising: administering to the subject an effective amount of a pharmaceutical composition comprising a compound of Formula I, its stereoisomers, prodrugs, or pharmaceutically acceptable salts thereof and an antibiotic.

Yet another embodiment of the present disclosure also relates to a method for treatment of bacterial infection in a subject caused by a drug-resistant bacterium comprising: administering to the subject an effective amount of a pharmaceutical composition comprising a compound of Formula I, its stereoisomers, prodrugs, or pharmaceutically acceptable salts thereof and an antibiotic.

Yet another embodiment of the present disclosure also relates to a method for treatment of bacterial infection in a subject caused by a vancomycin-resistant bacterium comprising: administering to the subject an effective amount of a pharmaceutical composition comprising a compound of Formula I, its stereoisomers, prodrugs, or pharmaceutically acceptable salts thereof and an antibiotic.

Yet another embodiment of the present disclosure also relates to a method for treatment of bacterial infection in a subject caused by a methicillin-resistant bacterium comprising: administering to the subject an effective amount of a pharmaceutical composition comprising a compound of Formula I, its stereoisomers, prodrugs, or pharmaceutically acceptable salts thereof and an antibiotic.

Yet another embodiment of the present disclosure also relates to a method for treatment of bacterial infection in a subject caused by a carbapenem-resistant bacterium comprising: administering to the subject an effective amount of a pharmaceutical composition comprising a compound of Formula I, its stereoisomers, prodrugs, or pharmaceutically acceptable salts thereof and an antibiotic.

Yet another embodiment of the present disclosure also relates to a method for treatment of bacterial infection in a subject caused by a drug-resistant bacterium, wherein the bacterium comprises a vancomycin-resistant *Staphylococcus aureus*, a vancomycin-resistant *Enterococcus faecium* or a methicillin-resistant *Staphylococcus aureus* or a meropenem-resistant NDM-1 gene expressing gram negative pathogens, comprising: administering to the subject an effective amount of a pharmaceutical composition comprising a compound of Formula I, its stereoisomers, prodrugs, or pharmaceutically acceptable salts thereof and an antibiotic.

An embodiment of the present disclosure relates to a pharmaceutical composition comprising a metal coordination complex of a compound of Formula I, its stereoisomers, prodrugs, or pharmaceutically acceptable salts thereof, and a metal, and an antibiotic and a method of preparing the same.

Another embodiment of the present disclosure relates to a pharmaceutical composition comprising a metal coordination complex of a compound of Formula I, its stereoisomers, prodrugs, or pharmaceutically acceptable salts thereof, and a metal, and β-lactam antibiotic and a method of preparing the same.

Yet another embodiment of the present disclosure relates a pharmaceutical composition comprising a metal coordination complex of a compound of Formula I, its stereoisomers, prodrugs, or pharmaceutically acceptable salts thereof, and a metal, and meropenem antibiotic and a method of preparing the same.

Yet another embodiment of the present disclosure relates to a pharmaceutical composition comprising a metal coordination complex of a compound of Formula I, its stereoisomers, prodrugs, or pharmaceutically acceptable salts thereof, and a metal, and carbapenem.

An embodiment of the present disclosure also relates to a pharmaceutical composition comprising a metal coordination complex of a compound of Formula I, its stereoisomers, prodrugs, or pharmaceutically acceptable salts thereof, and a metal, and an antibiotic, for use as a medicament.

Another embodiment of the present disclosure also relates to a pharmaceutical composition comprising a metal coordination complex of a compound of Formula I, its stereoisomers, prodrugs, or pharmaceutically acceptable salts thereof, and a metal, and an antibiotic, for use in treatment of a bacterial infection.

Another embodiment of the present disclosure also relates to a pharmaceutical composition comprising a metal coordination complex of a compound of Formula I, its stereoisomers, prodrugs, or pharmaceutically acceptable salts thereof, and a metal, and an antibiotic, for use in treatment of a bacterial infection caused by *Mycobacterium tuberculosis*.

Yet another embodiment of the present disclosure also relates to a pharmaceutical composition comprising a metal coordination complex of a compound of Formula I, its stereoisomers, prodrugs, or pharmaceutically acceptable salts thereof, and a metal, and an antibiotic, for use in the treatment of diseases caused by gram positive bacteria.

Yet another embodiment of the present disclosure also relates to a pharmaceutical composition comprising a metal coordination complex of a compound of Formula I, its stereoisomers, prodrugs, or pharmaceutically acceptable salts thereof, and a metal, and an antibiotic, for use in the treatment of diseases caused by gram negative bacteria.

Yet another embodiment of the present disclosure also relates to a pharmaceutical composition comprising a metal coordination complex of a compound of Formula I, its stereoisomers, prodrugs, or pharmaceutically acceptable salts thereof, and a metal, and an antibiotic for use in treatment of a bacterial infection, wherein the bacterium comprises a vancomycin-resistant bacterium, a methicillin-resistant bacterium, or carbapenem-resistant bacterium.

Yet another embodiment of the present disclosure also relates to a pharmaceutical composition comprising a metal coordination complex of a compound of Formula I, its stereoisomers, prodrugs, or pharmaceutically acceptable salts thereof, and a metal, and an antibiotic for use in treatment of a bacterial infection, wherein the bacterium comprises a vancomycin-resistant *Staphylococcus aureus*, a vancomycin-resistant *Enterococcus faecium*, a methicillin-resistant *Staphylococcus aureus*, or a meropenem-resistant NDM-1 gene expressing gram negative pathogens.

Yet another embodiment of the present disclosure also relates to a method for treatment of bacterial infection in a subject comprising: administering to the subject an effective amount of a pharmaceutical composition comprising a metal coordination complex of a compound of Formula I, its stereoisomers, prodrugs, or pharmaceutically acceptable salts thereof, and a metal, and an antibiotic.

Yet another embodiment of the present disclosure also relates to a method for treatment of bacterial infection in a subject caused by a gram-positive bacterium comprising: administering to the subject an effective amount of a pharmaceutical composition comprising a metal coordination complex of a compound of Formula I, its stereoisomers, prodrugs, or pharmaceutically acceptable salts thereof, and a metal, and an antibiotic.

Yet another embodiment of the present disclosure also relates to a method for treatment of bacterial infection in a subject caused by a gram-negative bacterium comprising: administering to the subject an effective amount of a pharmaceutical composition comprising a metal coordination complex of a compound of Formula I, its stereoisomers, prodrugs, or pharmaceutically acceptable salts thereof, and a metal, and an antibiotic.

Yet another embodiment of the present disclosure also relates to a method for treatment of bacterial infection in a subject caused by a drug-resistant bacterium comprising: administering to the subject an effective amount of a pharmaceutical composition comprising a metal coordination complex of a compound of Formula I, its stereoisomers, prodrugs, or pharmaceutically acceptable salts thereof, and a metal, and an antibiotic.

Yet another embodiment of the present disclosure also relates to a method for treatment of bacterial infection in a subject caused by a vancomycin-resistant bacterium comprising: administering to the subject an effective amount of a pharmaceutical composition comprising a metal coordination complex of a compound of Formula I, its stereoisomers, prodrugs, or pharmaceutically acceptable salts thereof, and a metal, and an antibiotic.

Yet another embodiment of the present disclosure also relates to a method for treatment of bacterial infection in a subject caused by a methicillin-resistant bacterium comprising: administering to the subject an effective amount of a pharmaceutical composition comprising a metal coordination complex of a compound of Formula I, its stereoisomers, prodrugs, or pharmaceutically acceptable salts thereof, and a metal, and an antibiotic.

Yet another embodiment of the present disclosure also relates to a method for treatment of bacterial infection in a subject caused by a carbapenem-resistant bacterium comprising: administering to the subject an effective amount of a pharmaceutical composition comprising a metal coordination complex of a compound of Formula I, its stereoisomers, prodrugs, or pharmaceutically acceptable salts thereof, and a metal, and an antibiotic.

Yet another embodiment of the present disclosure also relates to a method for treatment of bacterial infection in a subject caused by a drug-resistant bacterium, wherein the bacterium comprises a vancomycin-resistant *Staphylococcus aureus*, a vancomycin-resistant *Enterococcus faecium* or a methicillin-resistant *Staphylococcus aureus* or a meropenem-resistant NDM-1 gene expressing gram negative pathogens, comprising: administering to the subject an effective amount of a pharmaceutical composition comprising a metal coordination complex of a compound of Formula I, its stereoisomers, prodrugs, or pharmaceutically acceptable salts thereof, and a metal, and an antibiotic.

The antibacterial activity of disclosed compound in the present invention was found to be 1.2 µM against vancomycin-resistant Enterococci (VRE) which is 700-fold more effective than vancomycin. Also, this compound resensitized meropenem to meropenem-resistant bacteria such as NDM-1 producing gram negative bacteria. This compound showed excellent in-vivo antibacterial activity in combination with meropenem in bacterial sepsis infection model caused by NDM-1 producing *K. pneumoniae*. These compounds are the first examples of a new generation of glycopeptide antibiotics that can be developed to tackle vancomycin-resistant enterococcal infections.

EXAMPLES

The following examples provide details concerning the synthesis, activities, and applications of the compounds of the present disclosure. It should be understood the following is representative only, and that the invention is not limited by the details set forth in these examples.

Materials:

All reagents were purchased from Sigma-Aldrich and SD Fine and used without further purification. Analytical thin layer chromatography (TLC) was performed on E. Merck TLC plates pre-coated with silica gel 60 $F_{254}$ (250 m thickness). Visualization was accomplished using UV light, potassium permangante and Iodine. Column chromatography was performed on silica gel (60-120 Å pore size). HPLC analysis was performed on a Shimadzu-LC 8A Liquid Chromatograph instrument ($C_{18}$ column, 10 mm diameter, 250 mm length) with UV detector monitoring at 270 nm. Nuclear magnetic resonance spectra were recorded on Bruker (AV-400) 400 MHz spectrometer in deuterated solvents. Mass spectra were obtained using 6538-UHD Accurate mass Q-TOF LC-MS instrument. Bacterial strains MRSA ATCC 33591, *E. faecalis* ATCC 51575, *E. faecium* ATCC 51559 and *K. pneumoniae* ATCC BAA2146 were obtained from ATCC (Rockville, Md.). Clinical isolates *K. pneumoniae* R3949, *K. pneumoniae* R3934, *E. coli* R3336 and *A. baumanii* R676 were obtained from National Institute of Mental Health and Neuro Sciences (NIMHANS), Bengaluru. Tryptic-soy agar media was used for all the bacteria. Eppendorf 5810R centrifuge was used. TECAN (Infinite series, M200 pro) Plate Reader was used to measure absorbance. CD-1 or BALB/c mice were used for in-vivo studies

Example 1

Dipicolyl-vancomycin conjugate (4) of the instant disclosure were synthesized by coupling carboxylic group of vancomycin with dipicolyl-1,6-hexadiamine (3) (Scheme 1) through amide coupling using O-benzotriazole-N,N,N',N'-tetramethyl-uronium-hexafluorophosphate (HBTU). The steps employed in the method of synthesizing dipicolyl-1,6-hexadiamine (3) are further elaborated below in Examples 1.1-1.2

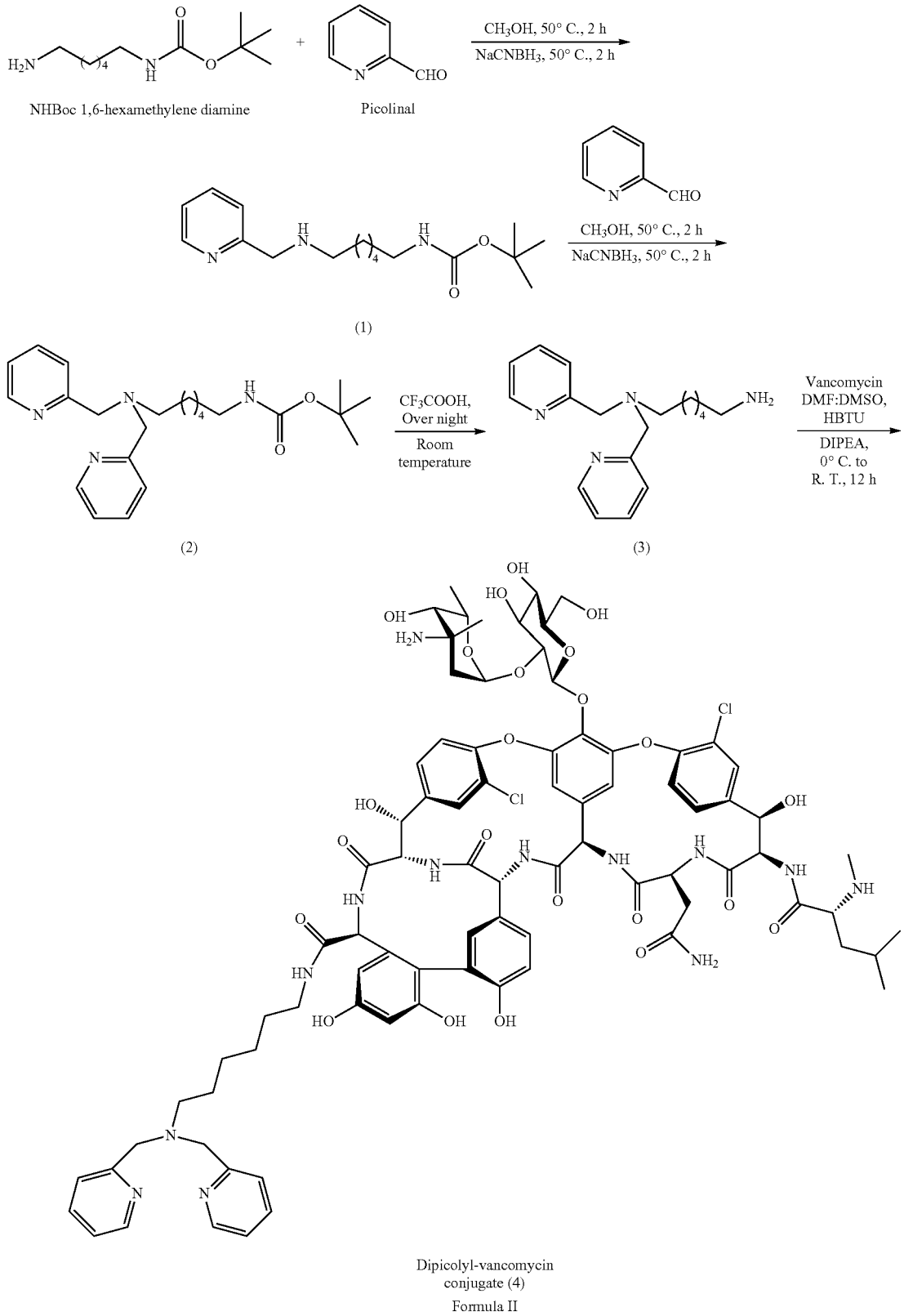

Scheme 1. Synthesis of dipicolyl-vancomycin conjugate (4)

Dipicolyl-vancomycin conjugate (4)
Formula II

Example 1.1: Synthesis of Dipicolyl-1,6-Hexadiamine (3)

1 equivalent of picolinal (1 g) was taken in 15 mL dry methanol and 1.2 equivalents of N-Boc hexanediamine (2.4 g) was added to it and the reaction mixture was kept for stirring at 50° C. for 2 h. Then the reaction was allowed to cool to room temperature and 1.5 equivalents of sodium cyanoborohydride ($NaCNBH_3$) was added to it. The reaction mixture was stirred at 50° C. for 2 h and then at room temperature for 12 h. Then, the crude product was subjected to HPLC and the required product (1) was obtained at retention time value of 11.0 min with a yield of 55%.

Product (1) Characterization:
$^1$H NMR (ppm, $D_2O$): 1.33 (s, 9H), 1.244-1.334 (m, 4H), 1.41-1.69 (m, 4H), 2.90-2.99 (t, 2H), 3.06-3.09 (t, 2H), 4.367 (s, 2H), 7.554-7.621 (m, 2H), 8.01-8.05 (m, 1H), 8.58-8.60 (m, 1H).
HRMS: m/z 308.3851 (observed); 308.2372 (calculated for (M+H)+).

The above mentioned procedure was repeated with 1.2 equivalents of picolinal and 1 equivalent of compound 1. Then product (2) was obtained with a yield of 63%.

Product (2) Characterization:
$^1$H NMR (ppm, $D_2O$): 1.40-1.48 (m, 4H), 1.498 (s, 9H), 1.844-2.02 (m, 4H), 2.91-2.98 (t, 2H), 3.143-3.238 (t, 2H), 4.367 (s, 2H), 7.468-7.554 (m, 4H), 7.90-7.99 (m, 2H), 8.53-8.59 (m, 2H).
HRMS: m/z 399.2747 (observed); 399.5571 (calculated for (M+H)+).

Then, compound 2 was dissolved in methanol and 5 mL of trifluoroacetic acid ($CF_3COOH$) was added to it and the reaction mixture was stirred at room temperature for 4 h. Then the solvent was evaporated and product (3) was obtained with quantitative yield of 95%.

Product (3) Characterization:
$^1$H NMR (ppm, $D_2O$): 1.372-1.437 (m, 4H), 1.678-1.862 (m, 4H), 3.10-3.14 (t, 2H), 3.24-3.29 (t, 2H), 4.518 (s, 4H), 7.445-7.518 (m, 4H), 7.86-7.957 (m, 2H), 8.58-8.60 (m, 2H).
HRMS: m/z 299.2222 (observed); 299.4371 (calculated for M+).

Example 1.2: Synthesis of Dipicolyl-Vancomycin Conjugate (4)

About 150 mg of vancomycin was dissolved in 1:1 mixture of dry dimethyl formamide (1 mL) dry dimethyl sulfoxide (1 mL). To this two equivalents (with respect to vancomycin) of dipicolyl-1,6-hexanediamine (3) in 1 mL of dry dimethylformamide was added. The reaction mixture was cooled to 0° C., and about 1.5 equivalents of 0.45 M HBTU solution in DMF was added followed by about 5.0 equivalents of diisopropylethylamine (DIPEA). The reaction mixture was then allowed to warm to room temperature and stirred for overnight. The product was purified by preparative reversed-phase HPLC using about 0.1% trifluoro acetic acid in $H_2O$/acetonitrile mixture (0-100%) as mobile phase and then lyophilized to afford tris-(trifluoroacetate) salts of dipicolyl-vancomycin conjugate (4) with 70% yield. $C_{18}$ column (10 mm diameter, 250 mm length) and UV detector (at 270 nm wave length) were used. The collected fractions, from HPLC were frozen by liquid $N_2$ and lyophilized using freeze dryer. This conjugate was characterized by $^1$H-NMR and HR-MS.

Dipicolyl-Vancomycin Conjugate (4) Characterization:
$^1$H-NMR (ppm, $D_2O$): 0.87-0.91 (m, 8H), 1.06 (bs, 4H), 1.23-1.38 (m, 4H), 1.48-1.53 (m, 2H), 1.69-1.74 (m, 3H), 1.90-1.92 (m, 1H), 2.32-2.33 (m, 2H), 2.66-2.67 (m, 2H), 2.73-2.78 (m, 2H), 2.88-3.03 (m, 9H), 3.52-3.54 (m, 2H), 3.67 (bs, 1H), 4.04-4.07 (m, 1H), 4.18 (bs, 1H), 4.67-4.68 (d, 1H), 4.86-4.89 (d, 1H), 5.10-5.17 (m, 3H), 5.24-5.35 (m, 4H), 5.45-5.48 (m, 1H), 5.90-5.95 (m, 1H), 6.71-6.85 (m, 2H), 6.95-7.37 (m, 6H), 7.47-7.55 (m, 8H), 7.84 (bs, 1H), 8.65-8.82 (bs, 1H), 8.95-9.09 (m, 2H).
HR-MS: m/z 865.8226 (observed), 865.8318 (calculated for $(M+2H)^{2+}$.

Example 2

Dipicolyl-Vancomycin-Zinc Complex (5):
About 10 mg of Dipicolyl-vancomycin conjugate (4) was dissolved in water. To this, one equivalent of zinc sulphate (0.9 mg) was added to it and mixed vigorously at room temperature for about 30 min. Then, dipicolyl-vancomycin-zinc complex (5) was characterized by HR-MS.
HR-MS: m/z 907.179 (observed), 906.535 (calculated for $M^{2+}$).

Dipicolyl-Vancomycin-Zinc Complex (6)
About 10 mg of Dipicolyl-vancomycin conjugate (4) was dissolved in water. To this, one equivalent of zinc sulphate (0.9 mg) was added to it and mixed vigorously at room temperature for about 1.5 h. Then, dipicolyl-vancomycin-zinc complex (6) was characterized by HR-MS.
HR-MS: m/z 914.46 (observed), 915.08 (calculated for $M^{2+}$).

Antibacterial Activity:
Minimum Inhibitory Concentration (MIC):

Test compounds were assayed in a micro-dilution broth format. Stock solutions were made by serially diluting the compounds using autoclaved millipore water or broth media. The antibacterial activity of the compounds was determined against gram positive bactreia like methicillin-resistant *S. aureus* (MRSA), vancomycin-intermediate-resistant *S. aureus* (VISA), vancomycin-sensitive *E. faecium* (VSE), vancomycin-resistant *E. faecalis* and vancomycin-resistant *E. faecium* (VRE). Antibacterial activity of dipicolyl-vancomycin conjugate conjugate (4) in combination with meropemem was determined against gram-negative bacteria such as *K. pneumoniae* ATCC BAA2146, clinical isolates *K. pneumoniae* R3949, *K. pneumoniae* R3934, *E. coli* R3336 and *A. baumanii* R676. Bacteria, to be tested, were grown for about 10 h in the suitable media, MRSA, VISA and gram negative bacteria were grown in Yeast-dextrose broth (about 1 g of beef extract, about 2 g of yeast extract, about 5 g of peptone and about 5 g of NaCl in about 1000 mL of sterile distilled water (pH-7)). For solid media, about 5% agar was used along with above mentioned composition. VSE and VRE were cultured in Brain Heart Infusion broth (Himedia). The bacterial samples were freeze dried and stored at −80° C. About 5 μL of these stocks were added to about 3 mL of the nutrient broth or Brain Heart Infusion broth and the culture was grown for about 6 h at about 37° C. prior to the experiments. This 6 h grown culture gives about $10^9$ cfu/mL and this was determined by spread plating method. The 6 h grown culture was diluted to give effective cell concentration of about $10^5$ cfu/mL which was then used for determining MIC. Compounds were serially diluted, in sterile water (2-fold dilution is employed) in a way that the working concentration was about 10 μM for MRSA, and VSE while for VRE, VISA and gram negative bacteria; it was about 100 μM. About 50 μL of these serial dilutions were added to the wells of 96 well plate followed by the addition of about 150 µL of bacterial solution. The plates were then incubated at about 37° C., 150 rpm in the incubator and O.D at 620 nm was recorded at an interval of about 24 h using TECAN (Infinite series, M200 pro) Plate Reader. Each concentration had triplicate values and the whole experiment was done at least twice and the MIC value was determined by taking the average of triplicate O.D. values for each concentration and plotting it against concentration. The data was then subjected to sigmoidal fitting. From the curve the MIC value was determined, as the point in the curve where the O.D. was similar to that of control having no bacteria.

The antibacterial activities of Dipicolyl-vancomycin conjugate (4), dipicolyl-1,6-hexadiamine (3) and vancomycin against Staphylococci (MRSA and VISA) and Enterococci (VREm and VREs) were summarized in Table 1. Compound 4 showed similar or slightly better activity than vancomycin against MRSA. Most exciting results were obtained in case of vancomycin-resistant Enterococci. When tested against highly pathogenic VREm, compound 4 exhibited the minimum inhibitory concentration (MIC) of 1.2 µM which is about 700-fold more active than vancomycin. Further, compound 4-zinc complex (compound 5) showed even much better activity against VREm which is about 1250-fold more than vancomycin. In contrast to compound 4, compound 3 did not show any activity against any of the bacteria tested.

In the present invention disclosure, the Dipicolyl-vancomycin conjugate is developed using facile synthetic methodology. These vancomycin conjugates showed strong, broad-spectrum antibacterial activity and about 700-fold more active than parent drug, vancomycin against VRE. Thus, this strategy can be a promising approach to develop new generation of antibiotics to tackle multidrug-resistant bacterial infections.

TABLE 1

Antibacterial activities of vancomycin derivatives. [a]Methicillin-resistant *S. aureus* (ATCC 33591). [b]Vancomycin intermediate resistant *S. aureus*. [c]Vancomycin-sensitive *E. faecium* (ATCC 19634). [d]Vancomycin-resistant *E. faecium* (VanA, ATCC 51559). [e]Vancomycin-resistant *E. faecalis* (VanA, ATCC 51575).

| Drug | MIC (µM) | | | | |
|---|---|---|---|---|---|
|  | MRSA | VISA | VSEm | VREm | VREs |
| Vancomycin | 0.63 | 13 | 0.6 | 750 | 250 |
| 4 | 0.6 | 0.4 | 0.3 | 1.2 | 2.5 |
| 3 | >100 | >100 | >100 | >100 | >100 |
| 5 | 0.3 | 0.3 | 0.31 | 0.6 | 1.5 |

Then, the antibacterial activities of Dipicolyl-vancomycin conjugate (4) is checked in combination with meropenem against New-Delhi β-lactamase producing gram negative bacteria such as *K. pneumoniae* BAA2146, clinical isolates *K. pneumoniae* R3949, *K. pneumoniae* R3934, *E. coli* R3336 and *A. baumanii* R676. Results were summarized in Table 2. Compound 4 was able to resensitize the above mentioned meropenem-resistant NDM-1 bacteria to meropenem. In contrast to compound 4, compound 3 did not show any appreciable synergistic activity in combinaion with meropenem against any of the bacteria tested. Further we have also evaluated the antibacterial activity of dipicolyl-vancomycin conjugate (4) in presence of zinc sulphate, wherein it forms dipicolyl-vancomycin-zinc complex (5). This complex did not restore the activity of meropenem against NDM-1 Gram-negative pathogens.

TABLE 2

Antibacterial activities against meropenem-resistant gram negative bacteria.

| NDM-1 expressing bacteria | MIC of Meropenem (µg/mL) | | | |
|---|---|---|---|---|
|  | In presence of compound 4 at 12 µM | In absence of compound 4 | In presence of compound 5 at 12 µM | In absence of compound 5 |
| *Klebsiella pneumoniae* R3949 | 3.1 | >100 | >100 | >100 |
| *Klebsiella pneumoniae* R3934 | 3.1 | >100 | >100 | >100 |
| *Klebsiella pneumoniae* ATCC BAA2146 | 1.5 | >100 | >100 | >100 |
| *Escherichia coli* R3336 | 12 | >100 | >100 | >100 |

Example: 3

In-Vivo Activity Against Meropenem-Resistant NDM-1 *K. pneumoniae* R3934:

Sepsis infection model: About six-week-old, female CD-1 mice (weight, ~19-24 g) were used for the experiments. Mice were infected intraperitoneally (i.p.) with a dose of ~$10^6$ CFU/mouse of meropenem-resistant NDM-1 *K. pneumoniae* R3934. Then, mice were treated twice at 1 h and 24 h post-infection with a specified i.p. dose of either saline, meropenem (10 mg/kg), compound 4 (10 mg/kg), or a combination of compound 4 (10 mg/kg) and meropenem (10 mg/kg). Here, colistin (5 mg/kg) was used as a positive control. Mice were euthanized after 48 h post-infection and then liver, spleen, kidney and lungs were collected to find out the bacterial density in these organs. Organs were placed into 10 ml sterile saline on ice, and then homogenized. The dilutions of the homogenate were plated onto agar plates, which were incubated for 24 h at 37° C. The bacterial titer was expressed as $\log_{10}$ CFU/g of organ weight.

The in-vivo efficacy of compound 4 in combination with meropenem showed excellent antibacterial activity in sepsis model. The result was comparable with positive antibiotic, colistin. On the other hand, meropenem and compound 4 alone did not show any activity (FIG. 1).

Example: 4

In-Vivo Activity Against Vancomycin-Resistant Enterococci in Murine Models of Kidney Infection:

Female CD-1 mice 6 to 8 weeks of age and weighing 20 to 25 g were used in this study. On day −7, all mice were injected intravenously (i.v.) with 0.2 mL of 0.2% λ-carrageenan to increase their susceptibility to bacterial renal infection. λ-Carrageenan increases mice susceptibility to renal infection following i.v. injection, possibly by forming a lattice structure in renal tissue and forming a support structure for bacterial attachment and growth. Bacterial strains that fail to cause renal infection in normal mice produce significant renal infections in λ-carrageenan-treated mice. On day 0, all mice were injected i.v. with 0.2 mL of the bacterial culture (VREs ATCC 51575, $10^8$ CFU/mouse) through the tail vein. Four hours after the bacterial inoculation, mice were treated intraperitoneally (i.p.) with vancomycin, compound 4 and linezolid at 12 mg/kg of body weight or 0.2 mL of saline (0.9% NaCl) control (n=5). All the test compounds or saline were administered once daily for an additional two consecutive days for a total of three doses. All mice were sacrificed on day 3. Both kidneys from each mouse were removed aseptically and homogenized in 10 mL of saline. The dilutions of the homogenate were plated onto sheep blood agar plates, which were incubated overnight at about 37° C. The bacterial titer was expressed as $\log_{10}$ CFU/g of kidney weight.

Figure 2:
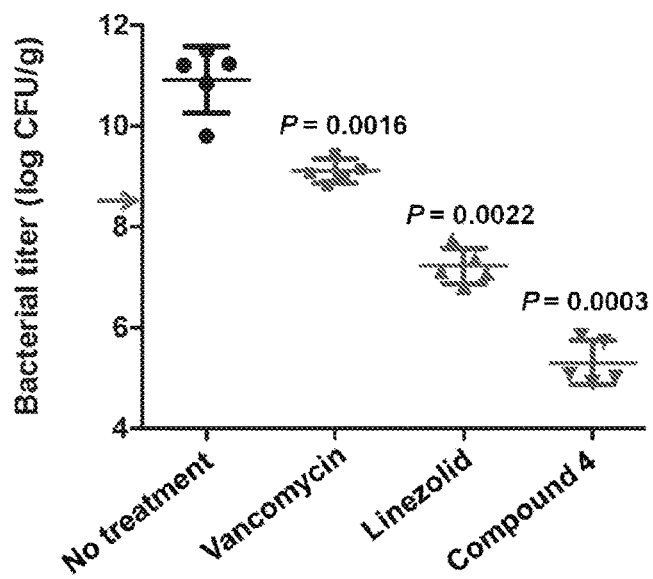
FIG. 2 illustrates in-vivo antibacterial activity of vancomycin, linezolid and compound 4 in murine renal infection model against VRE at 12 mg/kg.

The in-vivo activity of compound 4 was evaluated in a renal infection model against VRE. In comparison to vancomycin, compound 4 and linezolid reduced bacterial titer from the infected kidneys more effectively. Linezolid produced ~4 $\log_{10}$ CFU reduction compared to vehicle treated control (saline) whereas compound 4 produced ~5.0 $\log_{10}$ CFU reduction (FIG. 2). Solid arrow indicates bacterial pre-treatment titer (~8.0 $\log_{10}$ CFU/g). Five mice were used in each group. Statistical analysis was performed using Student's t-test. Differences are considered statistically significant from untreated group with a value of P<0.05 with 95% confidence intervals.

Example: 5

In-Vivo Toxicology:

To evaluate maximum tolerability of the new glycopeptide, systemic toxicity was performed on CD-1 female mice. Each mouse was injected with a 0.2 mL of freshly prepared compound 4 solution in saline. The dose of the compound administered was 100 mg/kg (n=5). Animals were directly inspected for adverse effects for 4 h, and mortality was observed for 14 days. All the mice were found to survive at 14 days indicating the high tolerability of compound 4 in animals with $LD_{50}$>100 mg/kg.

Example: 6

NDM-1 Enzyme Inhibition:

The NDM-1 was produced by *E. coli* BL21 (DE3) carrying pET30a-NDM-1 in LB medium. Initially, the purified NDM-1 enzyme (5 nM, HEPES buffer, pH-7.4) was supplemented with 20 µM $ZnSO_4$ for 30 min. Next, the enzyme was pre-incubated with the inhibitor (compound 4) for 20 min prior to the initiation of the assay by the addition of the substrate (Nitrocefin, 30 µM). Assays were read in 96-well microplate format at 490 nm (absorbance) using TECAN plate reader (Infinite Pro.) at 37° C. $IC_{50s}$ were deduced from a plot of percent loss of activity versus inhibitor concentration.

Figure 3:
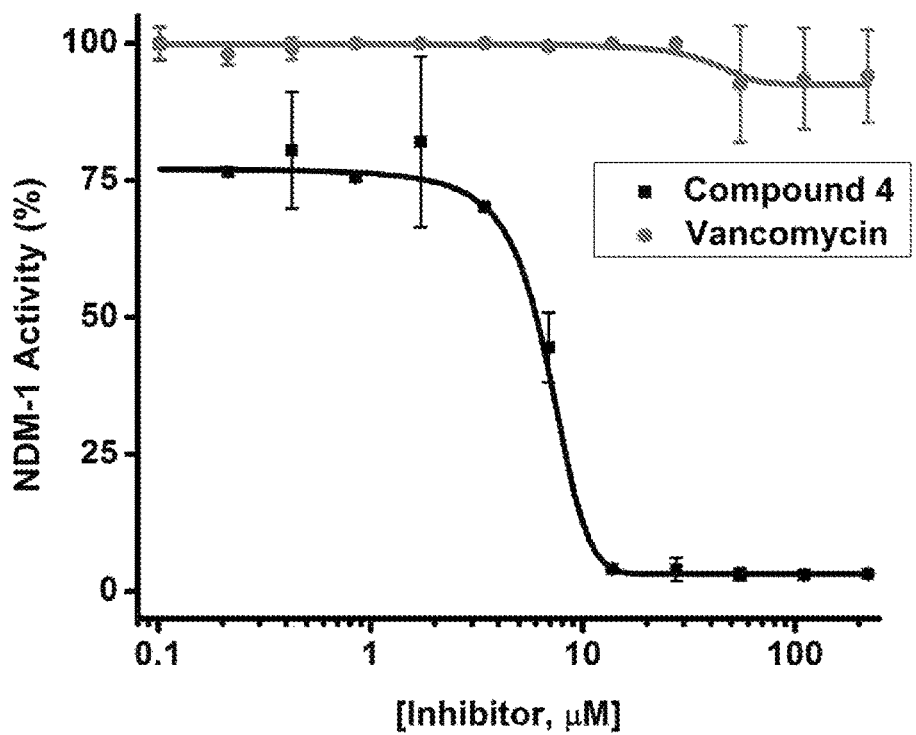
FIG. 3 illustrates NDM-1 enzyme inhibition by compound 4 ($IC_{50}$~6 μM).

To check the effect of compound 4 on NDM-1 activity, NDM-1 inhibition assay was performed in presence of inhibitors (compound 4 and vancomycin) using nitrocefin as a substrate. The results demonstrate that compound 4 showed potent in-vitro dose-dependent inhibition of NDM-1 (FIG. 3) with the $IC_{50}$ of ~6 µM whereas vancomycin had no effect on the activity of NDM-1.

Example: 7

Cell Wall Biosynthesis Inhibition:

In order to investigate whether the new installed properties of vancomycin derivative on inhibition of cell wall (peptidoglycan) biosynthesis against VRE, the accumulation of UDP-linked peptidoglycan precursor, UDP-N-acetyl-muramyl-pentadepsipeptide (UDPMurNAc-pp) was determined after treating the bacteria (VRE) with test compounds. Analysis of the cytoplasmic peptidoglycan nucleotide precursor pool was examined using VRE cells grown in 25 mL MHB. Cells were grown to an $A_{600\ nm}$ ($OD_{600}$) of 0.6 and incubated with 130 µg/mL of chloramphenicol for 15 min. Then, test compounds vancomycin (5 µM), compound 4 and physical mixture of compound 4 with zinc sulphate (5 µM) were added and incubated for another 60 min. Cells were collected and washed with sterile water to remove the antimicrobial agents and then extracted with boiling water. The cell extract was then centrifuged and the supernatant lyophilized. Then, the lyophilized powder was dissolved in 2 mL of water and pH was adjusted to 2.0 with 20% phosphoric acid. Now, the UDP-linked cell wall precursors in the solution were analyzed by RP-HPLC monitoring the UV absorbance peak at 260 nm wavelength and confirmed by HR-MS mass spectrometry.

Figure 4:
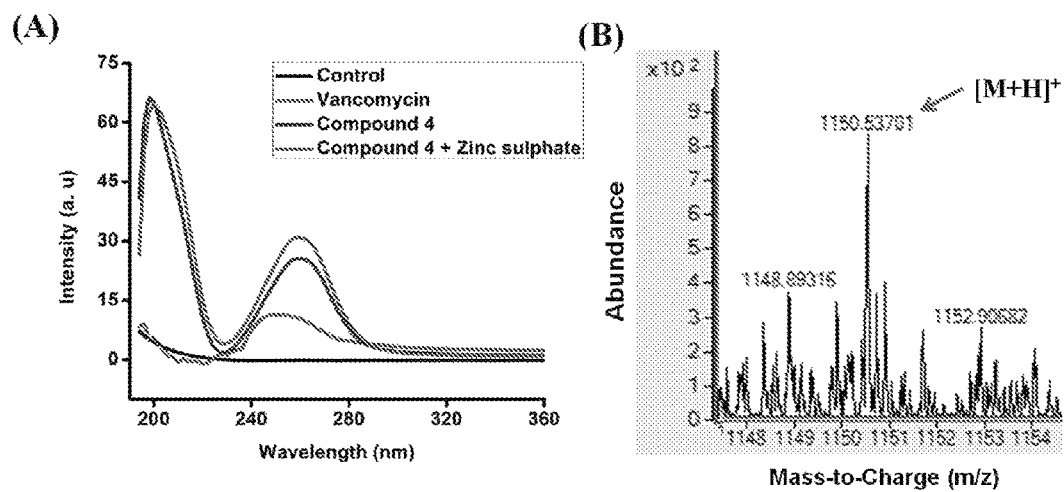
FIG. 4 illustrates (A) identification of intracellular UDP-MurNAc-pentadepsipeptide by monitoring absorbance at 260 nm wavelength; (B) identification of UDP-MurNAc-pentadepsipeptide by mass spectrometry as indicated by the peak at m/z 1150.53.

In case of compound 4, a more intense peak was observed at 260 nm compared to vancomycin, which corresponds to accumulation of UDPMurNAc-pp and confirmed by high-resolution mass spectrometry (m/z=1150.94 (cal), 1150.53 (obs) for [M+H]+). The result suggests that compound 4 showed greater cell wall biosynthesis inhibition compared to vancomycin. Further, compound 4 showed enhanced cell wall biosynthesis inhibition in presence of $Zn^{2+}$ (FIG. 4).

Example: 7

Figure 5:
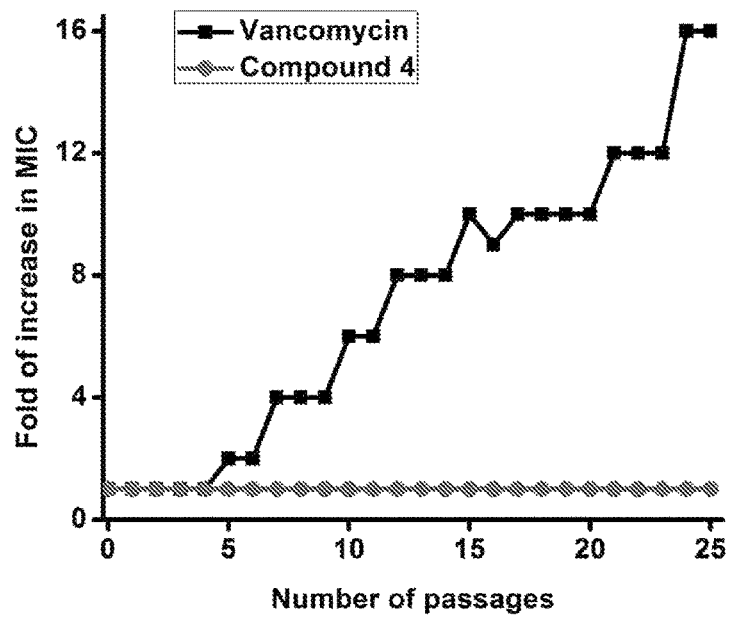
FIG. 5 illustrates bacterial resistance development study of vancomycin and compound 4 against MRSA.

Resistance Development Study:

MIC values of the compound 4 and vancomycin were determined against MRSA as described above. For the next day MIC experiment, the bacterial dilution was made by using the bacteria from sub-MIC concentration of the compounds (at MIC/2). Then, the concentration of this bacteria was adjusted to ~$10^5$ CFU/mL based on $OD_{600}$ and subjected to next MIC assay. After a 24 h incubation period, again bacterial dilution was prepared by using the bacterial suspension from sub-MIC concentration of the compound (at MIC/2) and assayed for another MIC experiment. The process was repeated for 25 passages, and the fold increase in MIC was determined. The results indicate the fold of increase in MIC every day. The results indicate that even after 25 serial passages, the MIC of compound 4 remained the same. However, in case of vancomycin, the MIC value started increasing after 7 passages and the value increased to ~16-fold after 25 passages (FIG. 5). Thus bacteria were unable in acquiring resistance to this compound and this emphasizes the longevity of such compounds in clinics.

Advantage

The above mentioned implementation examples as described on this subject matter and its equivalent thereof have many advantages, including those which are described.

The disclosed compounds and/, its stereoisomers, prodrugs, or pharmaceutically acceptable salts, and metal coordination complexes thereof described the present disclosure can provide better interaction with the cell wall of the bacteria. This increased association with bacterial cell wall precursors can serve as to inhibit the cell wall biosynthesis in both sensitive and resistant bacteria.

Although the subject matter has been described in considerable details with reference to certain preferred embodiments thereof, other embodiment are possible. As such, spirit and scope of the appended claims should not be limited to the description of the preferred embodiments contained therein.

REFERENCES

1) N. Woodford, D. M. Livermore, Infections caused by gram positive bacteria: A review of the global challenge. *J. Infect.* 59, S4-S16 (2009).
2) D. Kahne, C. Leimkuhler, W. Lu, C. T. Walsh, Glycopeptide and lipopeptide antibiotics. *Chem. Rev.* 105, 425-448 (2005).
3) C. K. Naber, *Staphylococcus aureus* bacteremia: Epidemiology, pathophysiology, and management strategies. *Clin. Infect. Dis.* 48, S231-S237 (2009).
4) C. T. Walsh, S. L. Fisher, I. S. Park, M. Prahalad, Z. Wu, Bacterial resistance to vancomycin: Five genes and one missing hydrogen bond tell the story. *Chem. Biol.* 3, 21-28 (1996).

5) L. Cui, X. Ma, K. Sato, K. Okuma, F. C. Tenover, E. M. Mamizuka, C. G. Gemmell, M. N. Kim, M. C. Ploy, N. El-Solh, V. Ferraz, K. Hiramatsu, Cell wall thickening is a common feature of vancomycin resistance in *Staphylococcus aureus*. *J. Clin. Microbiol.* 41, 5-14 (2003).
6) A. Y. Peleg, D. C. Hooper, Hospital-acquired infections due to gram negative bacteria. N. Engl. J. Med. 362, 1804-1813 (2010).
7) Antimicrobial resistance: global report on surveillance. World health Organization. Geneva. 2014.

We claim:

1. A compound of Formula I

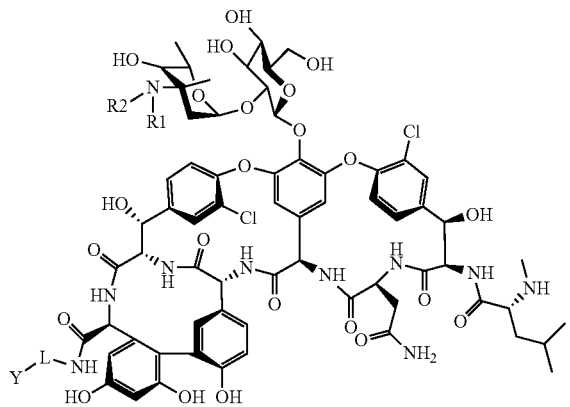

Formula I its stereoisomers, prodrugs, or pharmaceutically acceptable salts thereof:

wherein $R^1$ and $R^2$ are independently selected from hydrogen, substituted or unsubstituted $C_1$-$C_{18}$ aliphatic radical, or substituted or unsubstituted $C_4$-$C_{18}$ aromatic radical;

L is selected from substituted or unsubstituted $C_6$ aliphatic radical; and

Y is selected from $NR^3R^4$, or substituted $C_4$-$C_{18}$ aromatic radical, wherein $R^3$ and $R^4$ are independently selected from substituted $C_1$-$C_{18}$ aliphatic radical, or substituted $C_4$-$C_{18}$ aromatic radical.

2. The compound as claimed in claim 1, wherein $R^1$ and $R^2$ are independently selected from hydrogen, unsubstituted $C_2$-$C_{10}$ aliphatic radical, or substituted or unsubstituted $C_4$-$C_{10}$ aromatic radical;

L is selected from substituted or unsubstituted $C_6$ aliphatic radical;

Y is selected from $NR^3R^4$, wherein $R^3$ and $R^4$ are independently selected from $C_1$-$C_3$ aliphatic radical substituted with $C_5$ heteroaryl.

3. The compound of claim 1, wherein the compound is a compound of Formula II

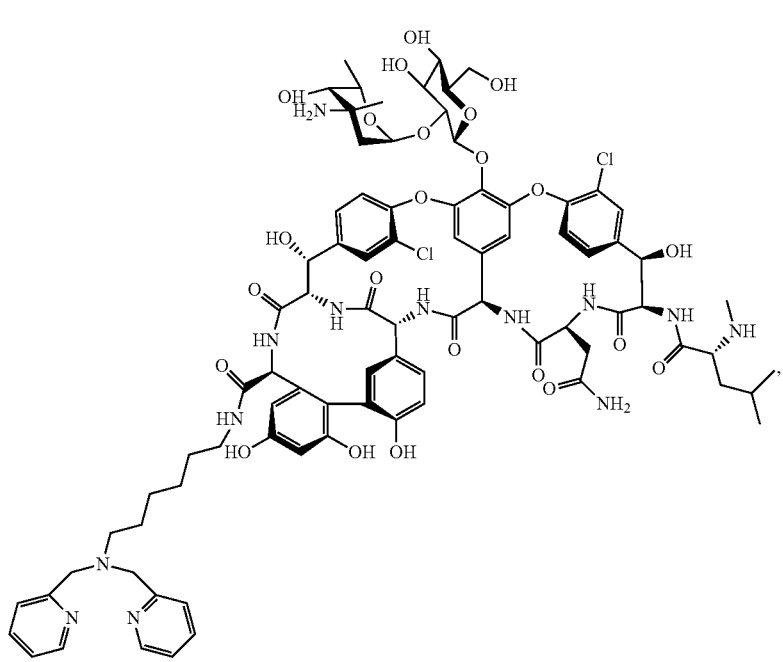

Formula II its stereoisomers, prodrugs, or pharmaceutically acceptable salts thereof.

4. A pharmaceutical composition comprising the compound as claimed in claim 1 and an antibiotic.

5. The pharmaceutical composition as claimed in claim 4, wherein the antibiotic is a β-lactam selected from the group consisting of penicillin, cephalosporin, carbapenem, monobactam and combinations thereof.

6. The pharmaceutical composition as claimed in claim 4, wherein the antibiotic is meropenem.

7. The pharmaceutical composition as claimed in claim 4 and further comprising a pharmaceutically acceptable carrier.

8. A metal coordination complex of a compound of Formula I

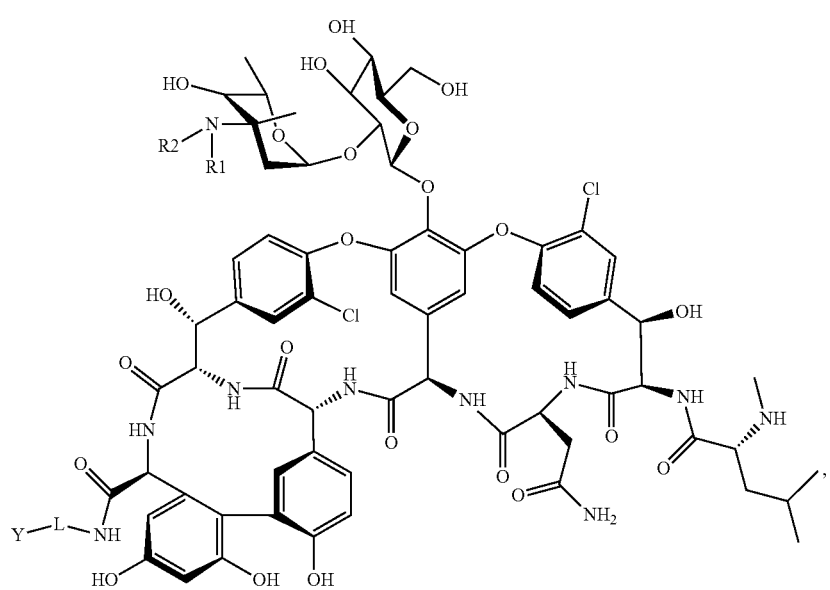

Formula I its stereoisomers, prodrugs, or pharmaceutically acceptable salts thereof, and a transition metal;
  wherein $R^1$ and $R^2$ are independently selected from hydrogen, substituted or unsubstituted $C_1$-$C_{18}$ aliphatic radical, or substituted or unsubstituted $C_4$-$C_{18}$ aromatic radical;
  L is selected from substituted or unsubstituted $C_6$ aliphatic radical; and
  Y is selected from $NR^3R^4$ or substituted $C_4$-$C_{18}$ aromatic radical, wherein $R^3$ and $R^4$ are independently selected from substituted $C_1$-$C_{18}$ aliphatic radical or substituted $C_4$-$C_{18}$ aromatic radical.

9. The metal coordination complex of the compound of Formula I as claimed in claim 8, wherein $R^1$ and $R^2$ are independently selected from hydrogen, substituted or unsubstituted $C_2$-$C_{10}$ aliphatic radical or substituted or unsubstituted $C_4$-$C_{10}$ aromatic radical;
  L is selected from substituted or unsubstituted $C_6$ aliphatic radical; and
  Y is selected from $NR^3R^4$, wherein $R^3$ and $R^4$ are independently selected from $C_1$-$C_3$ aliphatic radical substituted with $C_5$ heteroaryl; and the metal is zinc.

10. A method for treatment of bacterial infection in a subject comprising: administering to the subject an effective amount of the compound of claim 3.

11. The method as claimed in claim 10, wherein the bacterial infection is caused by a Gram positive bacterium or a Gram negative bacterium.

12. The method as claimed in claim 10, wherein the bacterial infection is caused by a vancomycin-resistant *Staphylococcus aureus*, a vancomycin-resistant *Enterococcus faecium*, a methicillin-resistant *Staphylococcus aureus*, or a carbapenem-resistant NDM-1 gene expressing Gram-negative pathogen.

13. The method as claimed in claim 10, wherein the bacterial infection is caused by a vancomycin-resistant *Staphylococcus aureus*, a vancomycin-resistant *Enterococcus faecium*, a methicillin-resistant *Staphylococcus aureus*, or a carbapenem-resistant NDM-1 gene expressing Gram-negative pathogen.

14. A method for treatment of bacterial infection in a subject comprising: administering to the subject an effective amount of the metal coordination complex of claim 8.

15. A method for treatment of bacterial infection in a subject comprising: administering to the subject an effective amount of the composition as claimed in claim 7.

16. A method for treatment of bacterial infection in a subject comprising: administering to the subject an effective amount of the compound of claim 1.

17. The method as claimed in claim 16, wherein the bacterial infection is caused by a Gram positive bacterium or a Gram negative bacterium.

* * * * *